US008143046B2

(12) United States Patent
Cervin et al.

(10) Patent No.: US 8,143,046 B2
(45) Date of Patent: *Mar. 27, 2012

(54) VARIANT *BUTTIAUXELLA* SP. PHYTASES HAVING ALTERED PROPERTIES

(75) Inventors: Marguerite A. Cervin, Redwood City, CA (US); Oliver Kensch, Bergheim (DE); Ulrich Kettling, Pulheim (DE); Steven S. Kim, Fremont, CA (US); Birgitta Leuthner, Lagenfeld (DE); Andrei Miasnikov, Mountain View, CA (US); Michael Ward, San Francisco, CA (US); Klaus Pellengahr, Cologne (DE)

(73) Assignee: Danisco US Inc., Genencor Division, Palo Alto, CA (US)

( * ) Notice: Subject to any disclaimer, the term of this patent is extended or adjusted under 35 U.S.C. 154(b) by 440 days.

This patent is subject to a terminal disclaimer.

(21) Appl. No.: 12/027,127

(22) Filed: Feb. 6, 2008

(65) Prior Publication Data
US 2009/0098249 A1 Apr. 16, 2009

Related U.S. Application Data

(63) Continuation-in-part of application No. 11/714,487, filed on Mar. 6, 2007.

(60) Provisional application No. 60/900,237, filed on Feb. 7, 2007, provisional application No. 60/905,222, filed on Mar. 6, 2007.

(51) Int. Cl.
*C12N 9/16* (2006.01)
(52) U.S. Cl. ........................................ 435/196; 424/94.6
(58) Field of Classification Search .................. None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio et al. |
| 4,366,241 | A | 12/1982 | Tom et al. |
| 4,683,202 | A | 7/1987 | Mullis et al. |
| 4,816,567 | A | 3/1989 | Cabilly et al. |
| 4,946,779 | A | 8/1990 | Kameda et al. |
| 5,605,793 | A | 2/1997 | Stemmer et al. |
| 5,650,322 | A | 7/1997 | Clarkson et al. |
| 5,674,707 | A | 10/1997 | Hintz et al. |
| 5,723,323 | A | 3/1998 | Kauffman et al. |
| 5,741,665 | A | 4/1998 | Kato et al. |
| 5,780,708 | A | 7/1998 | Lundquist et al. |
| 5,874,276 | A | 2/1999 | Fowler et al. |
| 6,022,725 | A | 2/2000 | Fowler et al. |
| 6,132,970 | A | 10/2000 | Stemmer et al. |
| 6,139,902 | A | 10/2000 | Kondo et al. |
| 6,221,644 | B1 | 4/2001 | Berka et al. |
| 6,235,517 | B1 | 5/2001 | Chu et al. |
| 6,255,098 | B1 | 7/2001 | Oh et al. |
| 6,268,328 | B1 | 7/2001 | Mitchinson et al. |
| 6,303,344 | B1 | 10/2001 | Patten et al. |
| 6,720,014 | B1 | 4/2004 | Short et al. |
| 6,777,589 | B1 | 8/2004 | Lundquist et al. |
| 6,803,499 | B1 | 10/2004 | Anderson et al. |
| 2003/0049815 | A1 | 3/2003 | Short et al. |
| 2004/0096850 | A1 | 5/2004 | Ravot |

FOREIGN PATENT DOCUMENTS

| | | |
|---|---|---|
| EP | 137 280 | 4/1985 |
| EP | 215 594 | 8/1986 |
| EP | 244 234 | 4/1987 |
| EP | 238 023 | 12/1993 |
| EP | 0813607 | 3/1996 |
| EP | 0813607 B | 3/1996 |
| EP | 1392353 | 3/2004 |
| EP | 0449375 | 5/2006 |
| EP | 1389915 | 9/2007 |
| WO | WO 92/18645 | 4/1991 |
| WO | WO9117243 | 11/1991 |
| WO | WO 96/00787 | 6/1995 |
| WO | WO0058517 | 10/2000 |
| WO | WO0134835 | 5/2001 |
| WO | WO 01/62947 A | 8/2001 |
| WO | WO02097130 | 12/2002 |
| WO | WO03012100 | 2/2003 |
| WO | WO03057247 | 7/2003 |
| WO | WO 2004/015084 | 2/2004 |
| WO | WO2004018674 | 3/2004 |
| WO | WO 2005/001036 | 5/2004 |
| WO | WO 2004/085638 | 10/2004 |
| WO | WO 2006/043178 | 10/2005 |
| WO | WO 2006/043178 A | 4/2006 |
| WO | WO 2008/097619 | 8/2008 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Cowieson et al., Poultry Science, 2005, 84: 1860-1867.*
Altschul, S. et al. "Basic Local Alignment Search Tool," *J. Mol. Biol.* 215:403-410, 1990.
Bajar, A., et al., "Identification of a fungal cutinase promoter that is inducible by a plant signal via a phosphorylated trans-acting factor," *Proc. Natl. Acad. Sci. USA*, vol. 88, pp. 8208-8212, Sep. 1991.
Berka et al., "*Aspergillus niger* var. awamori as a Host for the Expression of Heterologous Genes," in Kelly and Baldwin (eds.) *Applications of Enzyme Biotechnology*, New York: Plenum Press, 1991, pp. 273-292.
Beucage et al., "Deoxynucleoside Phosphoramidites: A New Class of Key Intermediates for Deoxypolynucleotide Synthesis" *Tetrahedron Letters* 22: 1859-1869, 1981.
Bhikhabhai, R. et al., "Isolation of Cellulolytic Enzymes from *Trichoderma reesei* QM 9414," *J. Appl. Biochem.* 6:336, 1984.
Boel, E. et al., "Two different types of intervening sequences in the glucoamylase gene from *Aspergillus niger,*" *The EMBO Journal*, vol. 3, No. 7, pp. 1581-1585, 1984.
Brisson, N. et al., "Expression of a bacterial gene in plants by using a viral vector," *Nature*, vol. 310, pp. 511-514, Aug. 9, 1984.

(Continued)

Primary Examiner — Richard Hutson
(74) Attorney, Agent, or Firm — Steptoe & Johnson LLP

(57) ABSTRACT

The present invention relates to variant phytase enzymes having altered properties.

17 Claims, 4 Drawing Sheets

OTHER PUBLICATIONS

Broglie, Richard et al., "Light-Regulated Expression of a Pea Ribulose-1,5-Bisphosphate Carboxylase Small Subunit Gene in Transformed Plant Cells," *Science*, vol. 224, pp. 838-843, 1984.
Brumbauer, A. et al. "Fractionation of cellulase and β-glucosidase in a *Trichoderma reesei* culture liquid by use of two-phase partitioning," *Bioseparation* 7:287, 1999.
Cadwell, R. et al. "Mutagenic PCR" *PCR Methods Appl.* 3:136-140, 1994.
Campbell et al., "Improved transformation efficiency of *Aspergillus niger*, using the homologous niaD gene for nitrate reductase," *Curr. Genet.*, vol. 16, pp. 53-56, 1989.
Cao, Q. et al. "Penicillopepsin-JT2, a recombinant enzyme from *Penicillium janthinellum* and the contribution of a hydrogen bond in subsite S3 to *kcat*" *Prot. Sci.* 9:991-1001, 2000.
Coruzzi, Gloria et al., "Tissue-specific and light-regulated expression of a pea nuclear gene encoding the small subunit of ribulose-1,5-biphosphate carboxylase," *The EMBO Journal*, vol. 3, No. 8, pp. 1671-1679, 1984.
Cromwell, G. et al. "Efficacy of phytase in improving the bioavailability of phosphorus in soybean meal and corn-soybean meal diets for pigs," *J. Anim. Sci.* 71(7):1831-1840, 1993.
de Groot, Marcel et al., "Agrobacterium tumefaciens-mediated transformation of filamentous fungi," *Nature Biotechnology*, vol. 16, pp. 839-842, 1998.
Deutscher, M. "Rethinking Your Purification Procedure," *Meth. Enzymol.* 182:779-780, 1990.
Ellouz, S. et al. "Analytical Separation of *Trichoderma reesei* Cellulases by Ion-Exchange Fast Protein Liquid Chromatography," *J. Chrom.* 396:307-317, 1987.
Finkelstein, "Transformation," in Finkelstein et al. (eds.) *Biotechnology of Filamentous Fungi*, Boston: Butterworth-Heinemann, ch. 6, pp. 113-156, 1992.
Fiske, Cyrus H. et al., "The Colorimetric Determination of Phosphorus," *The Journal of Biological Chemistry*, vol. 66, No. 2, pp. 375-392, 1925.
Fliess, A. "Characterization of Cellulases by HPLC Separation," *Eur. J. Appl. Microbiol. Biotechnol.* 17:314-318, 1983.
Fromm et al., "Inheritance and Expression of Chimeric Genes in the Progency of Transcgenic Maize Plants," *Biotechnology*, V. 8 pp. 833-839, Sep. 1990.
Gill et al., "Calculation of Protein Extinction Coefficients from Amino Acid Sequence Data," *Analytical Biochemistry*, 182:319-326 1989.
Goedegebuur, F. et al. "Cloning and relational analysis of 15 novel fungal endoglucanases from family 12 glycosyl hydrolase," *Curr. Gene.* 41:89-98 2002.
Goyal, A. et al. "Characteristics of Fungal Cellulases," *Biores. Tech.* 36:37-50, 1991.
Graessel, S. et al. "Regulated System for Heterologous Gene Expression in *Penicillium chrysogenum*," *Appl. Environ. Microbiol.* 63(2):753-756, 1997.
Harkki, A. et al., "A Novel Fungal Expression System: Secretion of Active Calf Chymosin from the Filamentous Fungus *Trichoderma reesei*," *Bio/Technology*, vol. 7, pp. 596-603, Jun. 1989.
Harkki, Anu et al., "Genetic engineering of *Trichoderma* to produce strains with novel cellulase profiles," *Enzyme Microb. Technol.*, vol. 13, pp. 227-233, Mar. 1991.
Heinonen et al., "A New and Convenient Colorimetric Determination of Inorganic Orthophosphate and Its Application to the Assay of Inorganic Pyrophosphatase," *Analytical Biochemistry*, V. 113, pp. 313-317 1981.
Hondel, C. van den et al. "Heterologous Gene Expression in Filamentous Fungi," in Bennett and Lasure (Eds.) *More Gene Manipulations in Fungi*, Academic Press, pp. 396-428, 1991.
Ilmen, M. et al., "Regulation of Cellulase Gene Expression in the Filamentous Fungus *Trichoderma reesei*," *Appl. Environ. Microbiol.* 63:1298-1306 1997.
Innis, M. A. et al., "Expression, Glycosylation, and Secretion of an *Aspergillus glucoamylase* by *Saccharomyces cerevisiae*," *Science*, vol. 228, pp. 21-26, 1985.
Kelly, J. et al. "Transformation of *Aspergillus niger* by the amdS gene of *Aspergillus nidulans*" *EMBO J.* 4:475-479 1985.
Korenegay, E. et al. "Response of broilers to graded levels of microbial phytase added to maize-soybean-meal-based diets containing three levels of non-phytate phosphorous," *Brit. J. Nutr.* 75:839-852, 1996.
Leuker, C. et al. "Sequence and promoter regulation of the PCK1 gene encoding phosphoenolpyruvate carboxykinase of the fungal pathogen *Candida albicans*," *Gene*, 192:235-240 1997.
Liu, M. et al. "Conserved Fungal Genes as Potential Targets for Broad-Spectrum Antifungal Drug Discovery," *Eukary. Cell*, 5:638-649, 2006.
Matthes, H. et al. "Simultaneous rapid chemical synthesis of over one hundred oligonucleotides on a microscale," *EMBO J.* 3:801-895, 1984.
Medve, J. et al. "Ion-exchange chromatographic purification and quantitative analysis of *Trichoderma reesei* cellulases cellobiohydrolase I, II and endoglucanase II by fast protein liquid chromatography," *J. Chromatography A* 808:153, 1998.
Mitchell, David B. et al., "The phytase subfamily of histidine acid phosphatases: isolation of genes for two novel phytases from the fungi *Aspergillus terreus* and *Myceliophthora thermophila*," *Microbiology*, vol. 143, pp. 245-252, 1997.
Morinaga, Y. "Improvement of Oligonucleotide-Directed Site-Specific Mutagenesis Using Double-Stranded Plasmid DNA," *Bio/Tech.* 2:636-639, 1984.
Murry, L. E. "Genetic engineering," in *McGraw Hill Yearbook of Science and Technology*, New York: McGraw Hill, pp. 191-196, 1992.
Nelson, R. et al. "A General Method of Site-Specific Mutagenesis Using a Modification of the *Thermus aquaticus* Polymerase Chain Reaction," *Anal. Biochem.* 180:147-151, 1989.
Nevalainen, K. et al., "The Molecular Biology. of *Trichoderma* and its Application to the Expression of Both Homologous and Heterologous Genes," in Berka and Leong (eds.), *Molecular Industrial Mycology*, NY: Marcel Dekker Inc., pp. 129-148, 1992.
Nunberg, Jack H. et al., "Molecular Cloning and Characterization of the Glucoamylase Gene of *Aspergillus awamori*," *Molecular and Cellular Biology*, pp. 2306-2315, Nov. 1984.
Penttila, Merja et al., "A versatile transformation system for the cellulolytic filamentous fungus *Trichoderma reesei*," *Gene*, vol. 61, pp. 155-164, 1987.
Potrykus, I. et al. "Molecular and general genetics of a hybrid foreign gene introduced into tobacco by direct gene transfer," *Mol. Gen. Genet.* 199:169-177, 1985.
Pourquie, J. et al. "Scale up of Cellulase Production and Utilization," in Aubert, J.P. et al (eds.) *Biochemistry and Genetics of Cellulose Degradation*, Academic Press, pp. 71-86, 1988.
Rogers, S. et al. "Gene Transfer in Plants: Production of Transformed Plants Using Ti Plasmid Vecotrs," in Weissbach, A. et al. (eds.) *Methods for Plant Molecular Biology*, Academic Press, New York, N.Y., pp. 421-463, 1988.
Saiki, R. et al. "Primer-Directed Enzymatic Amplification of DNA with a Thermostable DNA Polymerase" *Sci.* 239:487-491, 1988.
Sarkar, G. et al. "The 'Megaprimer' Method of Site-Directed Mutagenesis," *Biotechniques* 8:404-407, 1990.
Sheir-Neiss, G. et al. "Characterization of the secreted cellulases of *Trichoderma reesei* wild type and mutants during controlled fermentations," *Appl. Microbiol. Biotechnol.* 20:46-53, 1984.
Smith, T. et al. "Comparison of Biosequences," *Advances in Appl. Math.* 2:482-489, 1981.
Takamatsu, Nobuhiko et al., "Expression of bacterial chloramphenicol acetyltransferase gene in tobacco plants mediated by TMV-RNA," *The EMBO Journal*, vol. 6, No. 2, pp. 307-311, 1987.
Tilbeurgh, H. van et al. "Separation of endo- and exo-type cellulases using a new affinity chromatography method," *FEBS Lett.* 16:215-218, 1984.
Tomaz, C. et al. "Studies on the chromatographic fractionation of *Trichoderma reesei* cellulases by hydrophobic interaction," *J. Chromatography A* 865:123-128, 1999.
Ward, M. et al. "Use of *Aspergillus* overproducing mutants, cured for integrated plasmid, to overproduce heterologous proteins" *Appl. Microbiol. Biotechnol.* 39:738-743, 1993.

Winter, J et al. "The expression of heat shock protein and cognate genes during plant development," *Results Probl. Cell Differ*. 17:85-105, 1991.

Yelton, M. Melanie et al., "Transformation of *Aspergillus nidulans* by using a trpC plasmid," *Proc. Natl. Acad. Sci.*, vol. 81, pp. 1470-1474, Mar. 1984.

International Search Report for International Application No. PCT/US2008/001646, mailed Aug. 20, 2009.

Ngo, et al., The Protein Folding Problem and Tertiary Structure Prediction (1994) Merz et al. (ed.) Birkhauser, Boston MA p. 433 and 492-495.

Hans E. Muller, et al., Emended Description of Buttiauxella Agrestis With Recognition of Six New Species of Buttiauxella and Two New Species of Kluyvera . . . , Int'l. J. of Systematic Bacteriology (1996) vol. 46, No. 1, p. 50-63.

Seong Jun Yoon, et al., Isolation and Identification of Phytase-Producing Bacterium, *Enterobacter* sp. 4, and Enzymatic Properties of Phytase Enzyme, Enzyme and Mircobial Technology (1996) vol. 18, p. 449-454.

Database Accession No. PREV200300308051 Abstract: Zinn, et al., Phytase Activity of Several Bacteria Groups, Biotekhnologiya (2003) vol. 13, p. 3-10 (English abstract on p. 10).

DATABASE UniProt: Q6U677: Abstract: Zinn, et al., Phytase, Jul. 5, 2004.

Purva Vats, et al., Production Studies and Catalytic Properties of Phytases (myo-inositolhexakisphosphate phosphohydrolases): on overview, Enzyme and Microbial Technology (2004) vol. 35, p. 3-14 .

Nickolay V. Zinin, et al., Gene Cloning, Expression and Characterization of Novel Phytase From Obesumbacterium Proteus, FEMS Microbiology Letters (2004) vol. 236, p. 283-290.

Ortwin Simon, et al., In Vitro Properties of Phytases From Various Microbial Origins, International Journal of Food Science and Technology (2002) vol. 37, p. 813-822.

Ashima Vohra, et al., Phytases: Microbial Sources, Production, Purification and Potential Biotechnological Applications, Critical Reviews in Biotechnology (2003) vol. 23, No. 1, p. 29-60.

Archer, D. et. al. (1997). The Molecular Biology of Secreted Enzyme Production by Fungi. Critical Reviews in Biotechnology, vol. 17, Num. 4, p. 273-306.

Ausubel, F. et. al. (1999). Sequence Similarity Searching Using the BLAST Family of Programs. Short Protocols in Molecular Biology, Fourth Edition, Chapter 18, p. 18-01-18-23.

Ausubel, F. et. al. (1999). Homology Searching. Short Protocols in Molecular Biology, Fourth Edition, Chapter 7, p. 7-58-7-60.

Beggs, J. (1978). Transformation of yeast by a replicating hybrid plamid. Nature, vol. 275, p. 104-109.

Berka, R. (1998). Molecular characterization and expression of a phytase gene from the thermophilic fungus thermomyces lanuginosus. Applied and Environmental Microbiology, vol. 64, No. 11, p. 4423-4427.

Bessette, P. et. al. (1999). Efficient Folding of Proteins with multiple Disulfide Bonds in the *Escherichia coli* cytoplasm. Department of Chemical Engineering and Institute for Cell and Molecular Biology, University of Texas, vol. 96, No. 24, p. 13703-13708.

Caruthers, M. H. et. al. (1980). New Chemical Methods for Synthesizing Polynucleotides. Nucleic Acids Research, Symposium Series, No. 7, p. 215-223.

Cereghino, J. et. al. (2000). Heterologous Protein Expression in the Methylotrophic Yeast *Pichia pastoris*. FEMS Microbiology Reviews, vol. 24, p. 45-66.

Christou, P. (1994). Genetic Engineering of Crop Legumes and Cereals: Current Status and Recent Advances. Agro-Food-Industry Hi-Tech, Mar./Apr. 1994, p. 17-27.

Cole, S.P.C. (1985). The Ebv-Hyberidoma Technique and Its Application to Human Lung Cancer. Monoclonal Antibodies and Cancer Therapy, p. 77-96.

Cote, R. (1983). Generation of Human Monoclonal Antibodies Reactive with Cellular Antigens. Immunology, vol. 80, p. 2026-2030.

Davis, R. et. al. (1971). Genetic and Microbiological Research Techniques for *Neurospora crassa*. Microbiological Techniques, vol. 17A, p. 79-143.

Devereux, J. et. al. (1984) A Comprehensive Set of Sequence Analysis Programs for the VAX. Nucleic Acids Research, vol. 12, No. 12, p. 387-395.

Greiner, R. et. al. (1993). Purification and Characterization of Two Phytases from *Escherichia coli*. Archives of Biochemistry and Biophysics, vol. 303, No. 1, May 15, p. 107-113.

Greiner, R. et. al. (1997). Purification and Characterization of a Phytase from *Klebsiella terrigena*. Archives of Biochemistry and Biophysics, vol. 341, No. 2, p. 201-206.

Higgins, D. et. al. (1988). Clustal: A Package for Performing Multiple Sequence Alignment on a Microcomputer. Gene, vol. 73, p. 237-244.

Hinchcliffe, E. et. al. (1993). Yeasts as a Vehicle for the Expression of Heterologous Genes. The Yeasts, vol. 5, $2^{nd}$ Edition, p. 325-356.

Hinnan, A., et. al. (1978). Transformation of yeast. Proceedings of the National Academy of Sciences of the USA, vol. 75, p. 1929-1933.

Holland, B. et. al. (1990). Secretion of heterologous proteins in *Escherichia coli*. Methods in Enzymology, vol. 182, p. 132-143.

Hollenberg, C. et. al. (1997). Production of recombinant proteins be methylotrophic yeasts. Current Opinions in Biotechnology, vol. 8, No. 5, p. 554-560.

Horn, T. et. al. (1980). Synthesis of oligonucleotides on cellulose. Part II: design and synthetic strategy to the synthesis of 22 oligodeoxynucleotides coding for Gastric Inhibitory Polypeptide (GIP). Nucleic Acids Research, Symposium Series, No. 7, p. 225-232.

Hornwell, D. (1995). The 'peptoid' approach to the design of non-peptide, small molecule agonists and antagonists of neuropeptides. Trends in Biotechnology, vol. 13, No. 4, p. 132-134.

Howson, S. J. et. al. (1983). Production of phytate-hydrolysing enzyme by some fungi. Enzyme Microbiology Technology, vol. 5, p. 377-382.

Huse, W. et. al. (1989). Generation of a large combinatorial library of the immunoglobulin repertoire in phage lambda. Science, vol. 256, p. 1275-1281.

Igbasan, F.A. et. al. (2000). Comparative studies on the in vitro properties of phytases from various microbial origins. Archives of Animal Nutrition, vol. 53, p. 353-373.

Ito, H. et. al. (1983). Transformation of Intact yeast cells treated with alkali cations. Journal of Bacteriology, vol. 153, No. 1, p. 163-168.

Kane, J. (1995). Effects of rare codon clusters on high-level expression of heterologous proteins in *Escherichia coli*. Current Opinion in Biotechnology, vol. 6, No. 5, p. 494-500.

Kerovuo et. al. (2000). Analysis of myo-inositol hexakisphosphate hydrolysis by *Bacillus phytase*: Indication of a novel reaction mechanism. Journal of Biochemistry, vol. 352, p. 623-628.

Kerovuo et. al. (1998). Isolation, characterization, molecular gene cloning and sequencing of a novel phytase from *Bacillus subtilis*. Applied and Environmental Microbiology, vol. 64, No. 6, p. 2079-2085.

Kim, H. et. al. (2003). Isolation and characterization of a phytase with improved properties from *Citrobacter braakii*. Biotechnology Letters, vol. 25, p. 1231-1234.

Koehler, G. et. al. (1975). Continuous cultures of fused cells secreting antibody of predefined specificity. Nature, vol. 256, p. 495-497.

Kozbor, D. et. al. (1983). The production of monoclonal antibodies from human lymphocytes. Immunology Today, vol. 4, No. 3, p. 72-79.

Lassen, S. et. al. (2001). Expression, gene cloning, and characterization of five phytases from four Basidiomycete fungi: *Peniophora lycii, Agrocybe pediade, A ceriosporasp.*, and *Trametes pubescens*. Applied and Environmental Microbiology, vol. 67, No. 10, p. 4701-4707.

Lavillie, E. et. al. (1995). Gene fusion expression systems in *Escherichia coli*. Current Opinion in Biotechnology, vol. 6, No. 5, p. 501-506.

Livingstone, C. et. al. (1993). Protein sequence alignments: a strategy for the-hierarchical analysis of residue conservation. Computer Application Bioscience, vol. 9, p. 745-756.

Morrison, S. et. al. (1984). Chimeric human antibody molecules: Mouse antigen-binding domains with human constant region domains. Proc. Natl. Acad. Sci. USA, Immunology, vol. 81, p. 6851-6855.

Needleman, S. et. al. (1970). A general method applicable to the search for similarities in the amino acid sequence of two proteins. Journal of Molecular Biology, vol. 48, p. 443-453.

Neuberger, M. et. al. (1984). Recombinant antibodies possessing novel effector functions. Nature, vol. 312, p. 604-608.

Potrykus, I. (1991). Gene transfer to plants: Assessment of published approaches and results. Annual Review of Plant Physiology and Plant Molecular Biology, vol. 42, p. 205-225.

Punt, P. et. al. (2002). Filamentous fungi as cell factories for heterologous protein production. Trends in Biotechnology, vol. 20, No. 5, p. 200-206.

Riccio, M.L. et. al. (1997). Expression cloning of different bacterial phosphatase-encoding genes by histochemical screening of genomic libraries onto an indicator medium containing phenolphthalein diphosphate and methyl green. Journal of Applied Microbiology, vol. 82, p. 177-185.

Schlemmer, U. et. al. (2001). Degradation of phytate in the gut of pigs—Pathway of gastrointestinal inositol phosphate hydrolysis and enzymes involved. Archives of Animal Nutrition.

Simon, R. et. al., (1992). Peptoids: A modular approach to drug discovery. Proc. Natl Acad Sci., vol. 89, No. 20, p. 9367-9371.

Takeda, S. et. al. (1985). Construction of chimaeric processed immunoglobulin genes containing mouse variable and human constant region sequence. Nature, vol. 314, p. 452-454.

Tatusova, T. et. al. (1999). A new tool for comparing protein and nucleotide sequences. FEMS Microbiology Letters, vol. 174, No. 2, p. 247-250.

Tatusova, T. et. al. (1999). Erratum to BLAST 2 Sequences, a new tool for comparing protein and nucleotide sequence. FEMS Microbiology Letters, vol. 177, No. 1, p. 187-188.

Taylor, W. (1986). The classification of Amino acid conservation. Journal of Theoretical Biology, vol. 119, p. 205-218.

Trueman, L. (1995). Heterologous Expression in Yeast. Molecular Biology, vol. 49, chap. 27, p. 341-354.

Turner, G. (1994). Vectors for genetic manipulation. Progress in Industrial Microbiology, vol. 29, chap. 24, p. 641-666.

Wodzinski, R. et. al. (1996). Phytase. Advances in Applied Microbiology, vol. 42, p. 263-302.

Wyss, M. et. al. (1999). Biochemical characterization of fungal phytases (myo-inositol hexakisphophotate phosphohydrolases): catalytic properties. Applied and Environmental Microbiology vol. 65, No. 2, p. 367-373.

Kim, et al., Biotechno Letters, vol. 25, p. 1231-1234, 2003.

Kim, et al., Biotechno Letters ,vol. 28, p. 33-38, 2006.

R.C. Cadwell, et al., Randomization of Genes by PCR Mutagenesis, PCR Methods and Applications, 1992, vol. 2, p. 28-33.

Moon-Soo K et al., Assembly of Mutations for Improving Thermo stability of *Escherichia coli* AppA2 Phytase, Applied Microbiology and Biotechnology ( 2008) vol. 79, No. 5, p. 751-758.

Lehmann, et al., The Consensus Concept for Thermostability Engineering of Proteins: Further Proof of Concept, Protein Engineering (2002) vol. 15, No. 5, p. 403-411.

Shi et al., A Novel Phytase Gene AppA From *Buttiauxella* sp. GC21 Isolated From Grass Carp Intestine, Aquaculture (2008) vol. 275, p. 70-75.

Sproer, et al., The Phylogenetic Position of Serratia, *Buttiauxella* and Some Other Genera of the Family Enterobacteriaceae, International Journal of Systematic Bacteriology (1999) vol. 49, p. 1433-1438.

* cited by examiner

**Polypeptide of the Phytase Gene from *Buttiauxella* P1-29 (SEQ ID NO:1)**

MTISAFNRKKLTLHPGLFVALSAIFSLGSTAYANDTPASGYQVEKVVILSRHGVRAPTK
MTQTMRDVTPNTWPEWPVKLGYITPRGEHLISLMGGFYRQKFQQQGILSQGSCPTPNSI
YVWADVDQRTLKTGEAFLAGLAPECHLTIHHQQDIKKADPLFHPVKAGTCSMDKTQVQQ
AVEKEAQTPIDNLNQHYIPFLALMNTTLNFSTSAWCQKHSADKSCDLGLSMPSKLSIKD
NGNKVALDGAIGLSSTLAEIFLLEYAQGMPQAAWGNIHSEQEWASLLKLHNVQFDLMAR
TPYIARHNGTPLLQAISNALNPNATESKLPDISPDNKILFIAGHDTNIANIAGMLNMRW
TLPGQPDNTPPGGALVFERLADKSGKQYVSVSMVYQTLEQLRSQTPLSLNQPAGSVQLK
IPGCNDQTAEGYCPLSTFTRVVSQSVEPGCQLQ

*FIG. 1A*

Variant BP-11 Phytase with His Tags on N-terminus (SEQ ID NO:4)

HHHHHHNDTPASGYQVEKVVILSRHGVRAPTKMTQTMRDVTPNTWPEWPVKLGYITPRGE
HLISLMGGFYRQKFQQQGILSQGSCPTPNSIYVWTDVDQRTLKTGEAFLAGLAPQCGLTI
HHQQNLEKADPLFHPVKAGICSMDKTQVQQAVEKEAQTPIDNLNQHYIPSLALMNTTLNF
SKSPWCQKHSADKSCDLGLSMPSKLSIKDNGNEVSLDGAIGLSSTLAEIFLLEYAQGMPQ
AAWGNIHSEQEWALLLKLHNVYFDLMERTPYIARHKGTPLLQAISNALNPNATESKLPDI
SPDNKILFIAGHDTNIANIAGMLNMRWTLPGQPDNTPPGGALVFERLADKSGKQYVSVSM
VYQTLEQLRSQTPLSLNQPAGSVQLKIPGCNDQTAEGYCPLSTFTRVVSQSVEPGCQLQ

*FIG. 1B*

Variant BP-17 Phytase (SEQ ID NO:3)

NDTPASGYQVEKVVILSRHGVRAPTKMTQTMRDVTPNTWPEWPVKLGYITPRGEHLISLM
GGFYRQKFQQQGILSQGSCPTPNSIYVWTDVAQRTLKTGEAFLAGLAPQCGLTIHHQQNL
EKADPLFHPVKAGICSMDKTQVQQAVEKEAQTPIDNLNQHYIPSLALMNTTLNFSKSPWC
QKHSADKSCDLGLSMPSKLSIKDNGNEVSLDGAIGLSSTLAEIFLLEYAQGMPQAAWGNI
HSEQEWALLLKLHNVYFDLMERTPYIARHKGTPLLQAISNALNPNATESKLPDISPDNKI
LFIAGHDTNIANIAGMLNMRWTLPGQPDNTPPGGALVFERLADKSGKQYVSVSMVYQTLE
QLRSQTPLSLNQPAGSVQLKIPGCNDQTAEGYCPLSTFTRVVSQSVEPGCQLQ

*FIG. 1C*

SEQUENCE LISTING

<160> NUMBER OF SEQ ID NOS: 14

<210> SEQ ID NO 1
<211> LENGTH: 446
<212> TYPE: PRT
<213> ORGANISM: Buttiauxella sp.

<400> SEQUENCE: 1

Met Thr Ile Ser Ala Phe Asn Arg Lys Lys Leu Thr Leu His Pro Gly
 1               5                  10                  15

```
Leu Phe Val Ala Leu Ser Ala Ile Phe Ser Leu Gly Ser Thr Ala Tyr
            20                  25                  30
Ala Asn Asp Thr Pro Ala Ser Gly Tyr Gln Val Glu Lys Val Val Ile
                35                  40                  45
Leu Ser Arg His Gly Val Arg Ala Pro Thr Lys Met Thr Gln Thr Met
 50                  55                  60
Arg Asp Val Thr Pro Asn Thr Trp Pro Glu Trp Pro Val Lys Leu Gly
 65                  70                  75                  80
Tyr Ile Thr Pro Arg Gly Glu His Leu Ile Ser Leu Met Gly Gly Phe
                    85                  90                  95
Tyr Arg Gln Lys Phe Gln Gln Gly Ile Leu Ser Gln Gly Ser Cys
                100                 105                 110
Pro Thr Pro Asn Ser Ile Tyr Val Trp Ala Asp Val Asp Gln Arg Thr
                115                 120                 125
Leu Lys Thr Gly Glu Ala Phe Leu Ala Gly Leu Ala Pro Glu Cys His
            130                 135                 140
Leu Thr Ile His His Gln Asp Ile Lys Lys Ala Asp Pro Leu Phe
145                 150                 155                 160
His Pro Val Lys Ala Gly Thr Cys Ser Met Asp Lys Thr Gln Val Gln
                    165                 170                 175
Gln Ala Val Glu Lys Glu Ala Gln Thr Pro Ile Asp Asn Leu Asn Gln
                180                 185                 190
His Tyr Ile Pro Phe Leu Ala Leu Met Asn Thr Thr Leu Asn Phe Ser
                195                 200                 205
Thr Ser Ala Trp Cys Gln Lys His Ser Ala Asp Lys Ser Cys Asp Leu
            210                 215                 220
Gly Leu Ser Met Pro Ser Lys Leu Ser Ile Lys Asp Asn Gly Asn Lys
225                 230                 235                 240
Val Ala Leu Asp Gly Ala Ile Gly Leu Ser Ser Thr Leu Ala Glu Ile
                    245                 250                 255
Phe Leu Leu Glu Tyr Ala Gln Gly Met Pro Gln Ala Ala Trp Gly Asn
                260                 265                 270
Ile His Ser Glu Gln Glu Trp Ala Ser Leu Leu Lys Leu His Asn Val
            275                 280                 285
Gln Phe Asp Leu Met Ala Arg Thr Pro Tyr Ile Ala Arg His Asn Gly
290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                    325                 330                 335
Ala Gly His Asp Thr Asn Ile Ala Asn Ile Ala Gly Met Leu Asn Met
                340                 345                 350
Arg Trp Thr Leu Pro Gly Gln Pro Asp Asn Thr Pro Pro Gly Gly Ala
            355                 360                 365
Leu Val Phe Glu Arg Leu Ala Asp Lys Ser Gly Lys Gln Tyr Val Ser
370                 375                 380
Val Ser Met Val Tyr Gln Thr Leu Glu Gln Leu Arg Ser Gln Thr Pro
385                 390                 395                 400
Leu Ser Leu Asn Gln Pro Ala Gly Ser Val Gln Leu Lys Ile Pro Gly
                405                 410                 415
Cys Asn Asp Gln Thr Ala Glu Gly Tyr Cys Pro Leu Ser Thr Phe Thr
                420                 425                 430
Arg Val Val Ser Gln Ser Val Glu Pro Gly Cys Gln Leu Gln
```

```
            435                 440                 445
```

<210> SEQ ID NO 2
<211> LENGTH: 413
<212> TYPE: PRT
<213> ORGANISM: Buttiauxella sp.

<400> SEQUENCE: 2

```
Asn Asp Thr Pro Ala Ser Gly Tyr Gln Val Glu Lys Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Glu Cys His Leu
            100                 105                 110

Thr Ile His His Gln Gln Asp Ile Lys Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
```

```
            370                 375                 380
Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 3
<211> LENGTH: 413
<212> TYPE: PRT
<213> ORGANISM: Buttiauxella sp.

<400> SEQUENCE: 3

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
```

-continued

```
                340                 345                 350
Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 4
<211> LENGTH: 419
<212> TYPE: PRT
<213> ORGANISM: Artificial
<220> FEATURE:
<223> OTHER INFORMATION: modified protein

<400> SEQUENCE: 4

His His His His His Asn Asp Thr Pro Ala Ser Gly Tyr Gln Val
1               5                   10                  15

Glu Lys Val Val Ile Leu Ser Arg His Gly Val Arg Ala Pro Thr Lys
            20                  25                  30

Met Thr Gln Thr Met Arg Asp Val Thr Pro Asn Thr Trp Pro Glu Trp
        35                  40                  45

Pro Val Lys Leu Gly Tyr Ile Thr Pro Arg Gly Glu His Leu Ile Ser
    50                  55                  60

Leu Met Gly Gly Phe Tyr Arg Gln Lys Phe Gln Gln Gly Ile Leu
65                  70                  75                  80

Ser Gln Gly Ser Cys Pro Thr Pro Asn Ser Ile Tyr Val Trp Thr Asp
                85                  90                  95

Val Asp Gln Arg Thr Leu Lys Thr Gly Glu Ala Phe Leu Ala Gly Leu
            100                 105                 110

Ala Pro Gln Cys Gly Leu Thr Ile His His Gln Gln Asn Leu Glu Lys
        115                 120                 125

Ala Asp Pro Leu Phe His Pro Val Lys Ala Gly Ile Cys Ser Met Asp
    130                 135                 140

Lys Thr Gln Val Gln Gln Ala Val Glu Lys Glu Ala Gln Thr Pro Ile
145                 150                 155                 160

Asp Asn Leu Asn Gln His Tyr Ile Pro Ser Leu Ala Leu Met Asn Thr
                165                 170                 175

Thr Leu Asn Phe Ser Lys Ser Pro Trp Cys Gln Lys His Ser Ala Asp
            180                 185                 190

Lys Ser Cys Asp Leu Gly Leu Ser Met Pro Ser Lys Leu Ser Ile Lys
        195                 200                 205

Asp Asn Gly Asn Glu Val Ser Leu Asp Gly Ala Ile Gly Leu Ser Ser
    210                 215                 220

Thr Leu Ala Glu Ile Phe Leu Leu Glu Tyr Ala Gln Gly Met Pro Gln
225                 230                 235                 240

Ala Ala Trp Gly Asn Ile His Ser Glu Gln Trp Ala Leu Leu Leu
                245                 250                 255

Lys Leu His Asn Val Tyr Phe Asp Leu Met Glu Arg Thr Pro Tyr Ile
            260                 265                 270

Ala Arg His Lys Gly Thr Pro Leu Leu Gln Ala Ile Ser Asn Ala Leu
        275                 280                 285

Asn Pro Asn Ala Thr Glu Ser Lys Leu Pro Asp Ile Ser Pro Asp Asn
    290                 295                 300
```

Lys Ile Leu Phe Ile Ala Gly His Asp Thr Asn Ile Ala Asn Ile Ala
305                 310                 315                 320

Gly Met Leu Asn Met Arg Trp Thr Leu Pro Gly Gln Pro Asp Asn Thr
            325                 330                 335

Pro Pro Gly Gly Ala Leu Val Phe Glu Arg Leu Ala Asp Lys Ser Gly
        340                 345                 350

Lys Gln Tyr Val Ser Val Ser Met Val Tyr Gln Thr Leu Glu Gln Leu
    355                 360                 365

Arg Ser Gln Thr Pro Leu Ser Leu Asn Gln Pro Ala Gly Ser Val Gln
370                 375                 380

Leu Lys Ile Pro Gly Cys Asn Asp Gln Thr Ala Glu Gly Tyr Cys Pro
385                 390                 395                 400

Leu Ser Thr Phe Thr Arg Val Val Ser Gln Ser Val Glu Pro Gly Cys
                405                 410                 415

Gln Leu Gln

<210> SEQ ID NO 5
<211> LENGTH: 1534
<212> TYPE: DNA
<213> ORGANISM: Buttiauxella sp.

<400> SEQUENCE: 5
tttcacatag caaacaacaa cgagacgaac tcgacgttac cgctttgctt ctggagtata      60
tttatcagac tcaaacaccc caagaaaag aggctgtaaa tgacgatctc tgcgtttaac     120
cgcaaaaaac tgacgcttca ccctggtctg ttcgtagcac tgagcgccat attttcatta     180
ggctctacgg cctatgccaa cgacactccc gcttcaggct accaggttga aaagtggta     240
atactcagcc gccacggggt gcgagcacca accaaaatga cacagaccat gcgcgacgta     300
acacctaata cctggcccga atggccagta aaattgggtt atatcacgcc acgcggtgag     360
catctgatta gcctgatggg cgggttttat cgccagaagt tcaacaaca gggcatttta     420
tcgcagggca gttgccccac accaaactca atttatgtct gggcagacgt tgatcagcgc     480
acgcttaaaa ctggcgaagc tttcctggca gggcttgctc cggaatgtca tttaactatt     540
caccaccagc aggacatcaa aaagccgat ccgctgttcc atccggtgaa agcgggcacc     600
tgttcaatgg ataaaactca ggtccaacag gccgttgaaa aagaagctca accccccatt     660
gataatctga atcagcacta tattcccttt ctggccttga tgaatacgac cctcaacttt     720
tcgacgtcgg cctggtgtca gaaacacagc gcggataaaa gctgtgattt agggctatcc     780
atgccgagca agctgtcgat aaaagataat ggcaacaaag tcgctctcga cggggccatt     840
ggcctttcgt ctacgcttgc tgaaattttc ctgctggaat atgcgcaagg gatgccgcaa     900
gcggcgtggg ggaatattca ttcagagcaa gagtgggcgt cgctactgaa actgcataac     960
gtccagtttg atttgatggc acgcacgcct tatatcgcca gacataacgg cacgccttta    1020
ttgcaggcca tcagcaacgc gctgaacccg aatgccaccg aaagcaaact gcctgatatc    1080
tcacctgaca ataagatcct gtttattgcc ggacacgata ccaatattgc caatatcgca    1140
ggcatgctca acatgcgctg gacgctacct gggcaacccg ataacacccc tccgggcggc    1200
gctttagtct ttgagcgttt ggccgataag tcagggaaac aatatgttag cgtgagcatg    1260
gtgtatcaga ctctcgagca gttgcgctcc caaacaccac ttagccttaa tcaacctgcg    1320
ggaagcgtac agctaaaaat tcctggctgt aacgatcaga cggctgaagg atactgcccg    1380
ctgtcgacgt tcactcgcgt ggttagccaa agcgtggaac caggctgcca gctacagtaa    1440

-continued

```
atatcagaca aaaaaaatgc cgctcgcgat taagcgaacg gcattacttc ctagcttccc   1500
agctcggatt agcatggcga gagccgaaaa actt                              1534
```

<210> SEQ ID NO 6
<211> LENGTH: 413
<212> TYPE: PRT
<213> ORGANISM: Buttiauxella sp.

<400> SEQUENCE: 6

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 7
<211> LENGTH: 1274
<212> TYPE: DNA
<213> ORGANISM: Artificial
<220> FEATURE:
<223> OTHER INFORMATION: modified protein

<400> SEQUENCE: 7
actagtgtcg ccgtggagaa gcgcaacgac accccgcca gcggctacca ggtcgagaag      60
gtcgtcatcc tcagccgcca cggcgtccgc gccccctacca agatgaccca gaccatgcgc    120
gacgtcaccc ccaacacctg gcccgagtgg cccgtcaagc tcggctacat caccccctcg    180
ggcgagcacc tcatcagcct catgggcggc ttctaccgcc agaagttcca gcagcagggc    240
atcctcagcc agggctcgtg ccccaccccc aacagcatct acgtctggac cgacgtcgcc    300
cagcgcaccc tcaagaccgg cgaggccttc ctcgccggcc tcgcccccca gtgcggcctc    360
accatccacc accagcagaa cctcgagaag gccgaccccc tcttccaccc cgtcaaggcc    420
ggcatctgca gcatggacaa gacccaggtc cagcaggccg tcgagaagga gcccagacc     480
cccatcgaca acctcaacca gcactacatc cccagcctcg ccctcatgaa caccacctc     540
aacttcagca gagcccctg gtgccagaag cacagcgccg acaagagctg cgacctcggc    600
ctcagcatgc ccagcaagct cagcatcaag gacaacggca cgaggtctc cctcgacggc    660
gctatcggcc tcagctccac cctcgccgag atcttcctcc tcgagtacgc ccagggcatg    720
cctcaggccg cctggggcaa catccacagc gagcaggagt gggcccctcct cctcaagctc    780
cacaacgtct acttcgacct catggagcgc accccctaca tcgcccgcca aagggcacc    840
cccctcctcc aggccatcag caacgccctc aaccccaacg ccaccgagag caagctcccc    900
gacatcagcc ccgacaacaa gatcctcttc atcgccggcc acgacaccaa catcgccaac    960
atcgccggca tgctcaacat cgctggacc ctccccggcc agcccgacaa cacccccct     1020
ggcggcgctc tcgtctttga gcgcctcgcc gacaagtccg gcaagcagta cgtcagcgtc   1080
agcatggtct accagaccct cgagcagctc cgcagccaga ccccctcag cctcaaccag    1140
cctgccggca cgtccagct caagatcccc ggctgcaacg accagaccgc cgagggctac    1200
tgccccctca gcaccttcac ccgcgtcgtc agccagagcg tcgagcccgg ctgccagctc    1260
cagtaaggcg cgcc                                                      1274

<210> SEQ ID NO 8
<211> LENGTH: 1256
<212> TYPE: DNA
<213> ORGANISM: Buttiauxella sp.

<400> SEQUENCE: 8
actagtaacg acaccccgc cagcggctac caggtcgaga aggtcgtcat cctcagccgc      60
cacggagtcc gcgcccccac caagatgacc cagaccatgc gcgacgtcac ccccaacacc   120
tggcccgagt ggcccgtcaa gctcggctac atcaccccc gcggcgagca cctcatcagc    180
ctcatgggcg gcttctaccg ccagaagttc agcagcagg gcatcctcag ccagggctcg    240

```
tgtcccaccc ccaacagcat ctatgtctgg ccgacgtcg accagcgcac cctcaagacc    300
ggcgaggcct tcctcgccgg cctcgccccc cagtgcggcc tcaccatcca ccaccagcag    360
aacctcgaga aggccgaccc cctcttccac cccgtcaagg ccggcacctg cagcatggac    420
aagacccagg tccagcaggc cgtcgagaag gaggcccaga cccccatcga caacctcaac    480
cagcactaca tcccctt cct cgccctcatg aacaccaccc tcaacttcag caccagcgcc    540
tggtgccaga agcacagcgc cgacaagagc tgcgacctcg gcctcagcat gcccagcaag    600
ctcagcatca aggacaacgg caacaaggtc gccctcgacg gcgctatcgg cctcagctcc    660
accctcgccg agatcttcct cctcgagtac gcccagggca tgcctcaggc tgcctggggc    720
aacatccaca gcgagcagga gtgggccagc ctcctcaagc tccacaacgt ccagttcgac    780
ctcatggccc gcaccccta catcgcccgc acaacggca ccccctcct ccaggccatc       840 agcaacgccc tcaaccccaa cgccaccgag agcaagctcc ccgacatcag ccccgacaac    900
aagatcctct tcatcgccgg ccacgacacc aacatcgcca catcgccgg catgctcaac    960 atgcgctgga cccctccccgg ccagcccgac aacaccccc ccggcggcgc tctcgtctt t   1020 gagcgcctcg ccgacaagtc cggcaagcaa tatgtctctg tcagcatggt ctaccagacc    1080
ctcgagcagc tccgcagcca gacccccctc agcctcaacc agcccgccgg cagcgtccag    1140
ctcaagatcc ccggctgcaa cgaccagacc gccgagggct actgcccct cagcaccttc     1200 acccgcgtcg tcagccagag cgtcgagccc ggctgccagc tccagtaagg cgcgcc        1256

<210> SEQ ID NO 9
<211> LENGTH: 45
<212> TYPE: DNA
<213> ORGANISM: Artificial
<220> FEATURE:
<223> OTHER INFORMATION: synthetic primer

<400> SEQUENCE: 9
cactactagt gtcgctgtgg agaagcgcaa cgacaccccc gccag                    45

<210> SEQ ID NO 10
<211> LENGTH: 6
<212> TYPE: PRT
<213> ORGANISM: Artificial
<220> FEATURE:
<223> OTHER INFORMATION: synthetic primer

<400> SEQUENCE: 10

Val Ala Val Glu Lys Arg
1               5

<210> SEQ ID NO 11
<211> LENGTH: 82
<212> TYPE: DNA
<213> ORGANISM: Artificial
<220> FEATURE:
<223> OTHER INFORMATION: synthetic primer

<400> SEQUENCE: 11
caccatgcag accttcggtg cttttctcgt ttccttcctc gccgccagcg gcctggccgc    60
ggccaacgac accccgcca gc                                              82

<210> SEQ ID NO 12
<211> LENGTH: 18
<212> TYPE: DNA
<213> ORGANISM: Artificial
<220> FEATURE:
<223> OTHER INFORMATION: synthetic primer
```

<400> SEQUENCE: 12
ccttactgga gctggcag                                                   18

<210> SEQ ID NO 13
<211> LENGTH: 22
<212> TYPE: DNA
<213> ORGANISM: Artificial
<220> FEATURE:
<223> OTHER INFORMATION: synthetic primer

<400> SEQUENCE: 13
gagttcggcg cgccttactg ga                                              22

<210> SEQ ID NO 14
<211> LENGTH: 1242
<212> TYPE: DNA
<213> ORGANISM: Artificial
<220> FEATURE:
<223> OTHER INFORMATION: modified protein

<400> SEQUENCE: 14
aacgacaccc ccgccagcgg ctaccaggtc gagaaggtcg tcatcctcag ccgccacggc      60
gtccgcgccc ctaccaagat gacccagacc atgcgcgacg tcaccccaa cacctggccc     120 gagtggcccg tcaagctcgg ctacatcacc cctcgcggcg agcacctcat cagcctcatg     180
ggcggcttct accgccagaa gttccagcag cagggcatcc tcagccaggg ctcgtgcccc     240 accccccaaca gcatctacgt ctggactgac gtcgcccagc gcaccctcaa gaccggcgag    300
gccttcctcg ccggcctcgc ccccagtgc ggcctcacca tccaccacca gcagaaacctc    360 gagaaggccg accccctctt ccaccccgtc aaggccggca tctgcagcat ggacaagacc     420
caggtccagc aggccgtcga gaaggaggcc cagaccccca tcgacaacct caaccagcac     480
tacatcccca gcctcgccct catgaacacc accctcaact tcagcaagag cccctggtgc     540
cagaagcaca gcgccgacaa gagctgcgac ctcggcctca gcatgcccag caagctcagc     600
atcaaggaca acggcaacga ggtctcc ctc gacggcgcta tcggcctcag ctccaccctc    660
gccgagatct tcctcctcga gtacgcccag ggcatgcctc aggccgcctg gggcaacatc     720
cacagcgagc aggagtgggc cctcctcctc aagctccaca cgtctacttt cgacctcatg     780
gagcgcaccc cctacatcgc ccgccacaag ggcaccccc tcctccaggc catcagcaac     840
gccctcaacc caacgccac cgagagcaag ctccccgaca tcagcccga caacaagatc      900 ctcttcatcg ccgccacga caccaacatc gccaacatcg ccggcatgct caacatgcgc     960 tggacccctcc ccggccagcc cgacaacacc cccctggcg gcgctctcgt ctttgagcgc    1020
ctcgccgaca agtccggcaa gcagtacgtc agcgtcagca tggtctacca gaccctcgag   1080
cagctccgca gccagacccc cctcagcctc aaccagcctg ccggcagcgt ccagctcaag   1140
atccccggct gcaacgacca gaccgccgag ggctactgcc ccctcagcac cttcacccgc   1200
gtcgtcagcc agagcgtcga gcccggctgc cagctccagt aa                      1242

VARIANT BUTTIAUXELLA SP. PHYTASES HAVING ALTERED PROPERTIES

This application claims priority to U.S. provisional applications 60/900,237, filed Feb. 7, 2007 and 60/905,222, filed Mar. 6, 2007 and is a Continuation-in-Part of U.S. patent application Ser. No. 11/714,487, filed Mar. 6, 2007, the contents of each are incorporated by reference in their entirety.

FIELD OF THE INVENTION

The present invention relates to variant *Buttiauxella* spp. phytases, nucleic acids encoding the phytases and method of heterologous expression. The phytases encompassed by the invention may be used in industrial applications including methods for starch liquefaction, alcohol fermentations and for enhancing phosphate digestion in foods and animal feeds.

BACKGROUND OF THE INVENTION

Phosphorus (P) is an essential element for growth. A substantial amount of the phosphorus found in conventional livestock feed, e.g., cereal grains, oil seed meal, and by products that originate from seeds, is in the form of phosphate which is covalently bound in a molecule known as phytate. The bioavailability of phosphorus in this form is generally quite low for non-ruminants, such as poultry and swine, because they lack digestive enzymes for separating phosphorus from the phytate molecule.

Several important consequences of the inability of non-ruminants to utilize phytate may be noted. For example, expense is incurred when inorganic phosphorus (e.g., dicalcium phosphate, defluorinated phosphate) or animal products (e.g., meat and bone meal, fish meal) are added to meet the animals' nutritional requirements for phosphorus. Additionally, phytate can bind or chelate a number of minerals (e.g., calcium, zinc, iron, magnesium, and copper) in the gastrointestinal tract, thereby rendering them unavailable for absorption. Furthermore, most of the phytate present in feed passes through the gastrointestinal tract, elevating the amount of phosphorus in manure. This leads to an increased ecological phosphorus burden on the environment.

Microbial phytase, as a feed additive, has been found to improve the bioavailability of phytate phosphorus in typical non-ruminant diets (See, e.g., Cromwell, et al, 1993). The result is a decreased need to add inorganic phosphorus to animal feeds, as well as lower phosphorus levels in the excreted manure (See, e.g., Kornegay, et al, 1996). In addition to a feed additive, phytases may be used for the production of low-phytin feed fractions. For example, phytases may be used in wet milling of grains for the production of e.g., low-phytin corn steep liquor and low-phytin corn gluten or in a dry milling process in combination with starch hydrolyzing enzymes for the production of glucose and alcohols (e.g., ethanol).

Despite the advantage of using phytases in these applications, surprisingly few known phytases have gained widespread acceptance in the feed, starch liquefaction and alcohol fermentation industries. The reasons for this vary from enzyme to enzyme. Typical concerns relate to high manufacturing costs and/or poor stability/activity of the enzyme in the environment of the desired application. A number of enzymatic criteria must be fulfilled by a phytase if it is to be attractive for widespread use in industrial applications. The more important enzymatic criteria include a high overall specific activity, a low pH optimum, resistance to gastrointestinal proteases and thermostability.

Thermostability is one of the most important prerequisites for successful application of phytase as a feed enzyme and for use in starch liquefaction processes because the phytase in the feed and/or processes are exposed to elevated temperatures. For example, in feed pelleting processes the temperatures are between 60 and 95° C. and in starch liquefaction processes the temperatures are between 75 to 120° C.

The DNA sequence of a *Buttiauxella* sp P1-29 gene which encodes a phytase was reported in WO 06/043178, published Apr. 27, 2006. Reference is made to SEQ ID NO: 1 and SEQ ID NO:2 and the amino acid sequence of the phytase gene of *Buttiauxella* sp P1-29 (SEQ ID NO:3) reported therein. Based on various intrinsic properties, the *Buttiauxella* sp P1-29 phytase represented an excellent starting point from which to begin a mutagenesis program for a thermostable phytase for various commercial applications. WO 06/043178 discloses numerous variants of the *Buttiauxella* sp P1-29 phytase (see, e.g., Table 1). At least one variant disclosed in WO 06/043178 and designated herein as BP-11 has been further modified. The present invention is directed to variants having altered properties, such as improved properties, including but not limited to a) improved thermostability, b) increased specific activity, and/or c) increased specific activity with retention of thermostability as compared to *Buttiauxella* sp P1-29 phytase or the BP-11 variant.

SUMMARY OF THE INVENTION

In one aspect, the invention relates to a phytase that is the expression product of a mutated DNA sequence encoding a phytase, the mutated DNA sequence being derived from a precursor of a *Buttiauxella* spp phytase. In one embodiment, the phytase is derived from *Buttiauxella* sp. strain P1-29.

In a further aspect, the invention relates to a phytase variant, said variant comprising a substitution corresponding to positions A122, D125, T167, F197, T209, A211, K240, A242, S281, Q289, A294 and N303 in a phytase derived from *Buttiauxella* sp strain P1-29.

In another aspect, the invention relates to an isolated phytase comprising a substitution corresponding to positions A122, D125, T167, F197, T209, A211, K240, A242, S281, Q289, A294 and N303 of SEQ ID NO:1 and having at least 95% sequence identity inclusive of the variant substitutions with amino acid residues 34-446 of SEQ ID NO:1. In one embodiment, the substitution comprises A122T, D125A, T167I, F197S, T209K, A211P, K240E, A242S, S281L, Q289Y, A294E and N303K of SEQ ID NO:1. In another embodiment the substitution corresponds to positions R51, R55, T58, K59, D125, R127, K164, N239, G248, T252, E255, E276, H286, F290, M293, N303, H339, D340, T341, and/or D361 of SEQ ID NO:1.

In an additional aspect, the invention relates to a variant of the phytase designated BP-1, said variant comprising a substitution corresponding to positions R24, R28, T31, K32, D98, R100, K137, N212, G221, T225, E228, E249, H259, F263, M266, N276, H312, D313, T314, and/or D334 of SEQ ID NO: 4. In one embodiment, the variant of BP-11 has a substitution at a position corresponding to D98. In a preferred embodiment, the substitution is D98A.

In yet another aspect, the invention relates to a polypeptide having phytase activity which comprises SEQ ID NO:3. In one embodiment, the invention relates to a polypeptide having phytase activity consisting of the amino acid sequence of SEQ ID NO:3.

In a further aspect, the invention relates to an isolated DNA encoding a phytase variant encompassed by the invention and expression vectors including said DNA.

In yet a further aspect, the invention relates to a variant *Buttiauxella* sp. having improved phytase characteristics. In one embodiment, the improved phytase characteristic will be enhanced thermal stability compared to a native *Buttiauxella* sp. and more specifically the *Buttiauxella* sp. phytase derived from strain P1-29. In other embodiments, the variant will have improved characteristics compared to BP-11.

In other aspects, the invention relates to enzyme compositions comprising a protein having phytase activity wherein the enzyme composition is used in commercial applications. In one embodiment, the enzyme composition may be an animal feed composition. In other embodiments, the enzyme composition may be used in starch hydrolysis (e.g. liquefaction) processes. In further embodiments, an enzyme composition comprising a phytase encompassed by the invention will include additional enzymes, such as glucoamylases, alpha amylases, protease, cellulases and combinations thereof.

In one aspect, the present invention relates to a fermentation medium including a *Buttiauxella* phytase or a variant thereof from a culture of filamentous fungal cells. In one aspect, the filamentous fungal cells are *Trichoderma* cells, such as *T. reesei*. In one aspect, the phytase has an amino acid sequence with at least 75% sequence identity with SEQ ID NO:1, such as SEQ ID NO:1, SEQ ID NO:2 or SEQ ID NO:3.

In a further aspect, the present invention relates to methods for producing a phytase in a filamentous fungal host cell by transforming a filamentous fungal host cell with a DNA construct including a promoter having transcriptional activity in the filamentous fungal host cell operably linked to a heterologous polynucleotide encoding a phytase having phytase activity and having an amino acid sequence with at least 75% sequence identity to SEQ ID NO: 1, cultivating the transformed filamentous fungal host cell in a suitable culture medium to allow expression of said phytase and producing the phytase. The method may also include recovering the produced phytase. In one embodiment, the filamentous fungal host cell is a *Trichoderma* cell, such as *T. reesei*. In one aspect, the phytase has at least 95% amino acid sequence identity with SEQ ID NO: 1. In a further aspect, the phytase has the sequence of SEQ ID NO:1, SEQ ID NO:2 or SEQ ID NO:3. In another aspect, the invention is a *Trichoderma* cell obtained according to the method outlined hereinabove.

BRIEF DESCRIPTION OF THE DRAWINGS

FIG. 1A depicts the polypeptide encoded by the phytase gene from *Buttiauxella* P1-29 (BP-WT) (SEQ ID NO:1) including the native signal sequence and the mature protein (SEQ ID NO:2). The signal sequence is underlined.

FIG. 1B depicts the mature protein of the variant BP-11 without a signal sequence but including N-terminal His tags (SEQ ID NO:4). The BP-11 variant has a substitution of 11 amino acid residues when aligned with the BP-WT. These substitutions are highlighted and underlined in the figure.

FIG. 1C depicts the mature protein of variant *Buttiauxella* phytase (BP-17) (SEQ ID NO:3). The BP-17 variant has the same 11 amino acid substitutions as BP-11 plus one (1) additional substitution, which is highlighted and underlined in the figure.

DETAILED DESCRIPTION OF THE INVENTION

Figure 2:
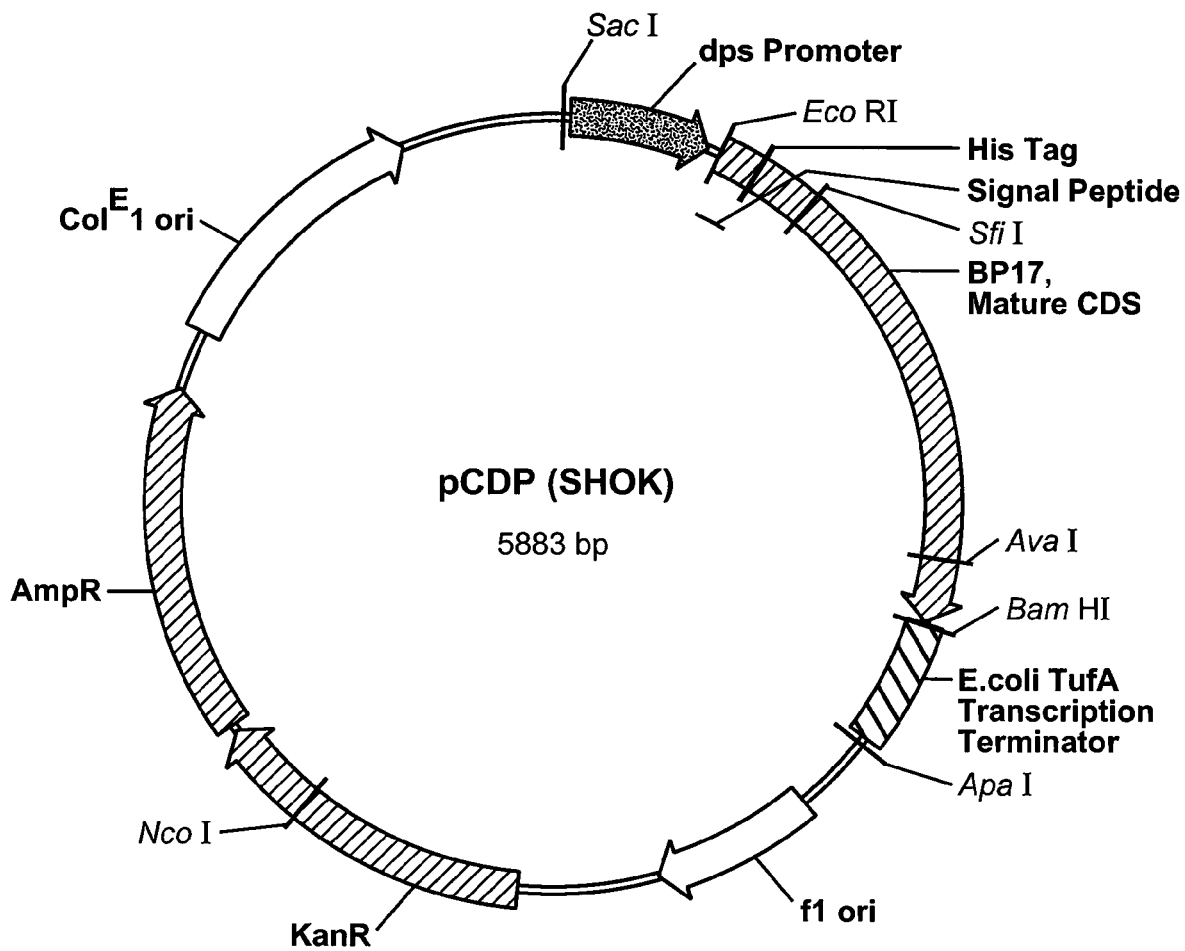
FIG. 2 illustrates expression vector pCDP(SHOK) as described more fully in Example 3.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention.

Although any methods and materials similar or equivalent to those described herein can be used in the practice or testing of the present invention, the preferred methods and materials are described. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

DEFINITIONS

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8 or EC number 3.1.3.26.

The term "a *Buttiauxella* spp. phytase", as used herein refers to a phytase protein obtained from a *Buttiauxella* spp. In one embodiment, the *Buttiauxella* spp. phytase comprises the amino acid sequence of NCIMB (National Collections of Industrial Marine and Food Bacteria, Scotland, UK) accession number NCIMB 41248. In a preferred embodiment, a *Buttiauxella* spp. phytase comprises the amino acid sequence of SEQ ID NO:2 or amino acid residues 34 to 446 of SEQ ID NO:1.

The term "corresponding to a *Buttiauxella* spp. phytase", as used herein, refers to an enzyme having the same functional characteristics or sequence of a *Buttiauxella* spp. phytase, but not necessarily obtained from a source of *Buttiauxella* spp.

The term "*Buttiauxella*" refers to a genus of gram negative, facultatively anaerobic bacteria of the family Enterobacteriaceae and *Buttiauxella* spp include *B. agrestis, B. brennerase, B. ferragutiae, B. gaviniae, B. izardii, B. noackiae*, and *B. warmboldiae*. Strains of the *Buttiauxella* species are available for example from the American Type Culture Collection (ATCC) and DSMZ, the German National Resource Centre for Biological Material.

The term "wild-type phytase" or "wild-type" refers to an enzyme with an amino acid sequence found in nature.

The term "variant *Buttiauxella* spp. phytase" means a phytase enzyme with an amino acid sequence derived from the amino acid sequence of a parent phytase or precursor phytase but differing by at least one amino acid substitution, insertion and/or deletion which together are referred to as mutations.

The term "mature phytase" refers to a phytase following signal processing, such as removal of secretion signal sequences.

The term "BP-11" denotes a phytase comprising the amino acid sequence of positions 7-419 of SEQ ID NO:4. BP-11 is a variant of a wild-type Buttiauxella spp. phytase having SEQ ID NO:1.

The term "BP-17" denotes a phytase comprising the amino acid sequence of SEQ ID NO:3.

"Protein", as used herein, includes proteins, polypeptides, and peptides. As will be appreciated by those in the art, the nucleic acid sequences of the invention, as defined below and further described herein, can be used to generate protein sequences.

The terms "amino acid residue equivalent to", "amino acid corresponding to" and grammatical equivalents thereof are used herein to refer to an amino acid residue of a protein having the similar position and effect as that indicated in a particular amino acid sequence of a particular protein. The person of skill in the art will recognize the equivalence of specified residues in comparable phytase proteins.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff ed., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (http://www.ncbi.nlm.nih.gov/).

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, pH activity profile, and ability to be secreted.

The terms "thermally stable" and "thermostable" refer to phytases of the present invention that retain a specified amount of enzymatic activity after exposure to elevated temperature.

The term "enhanced stability" in the context of a property such as thermostability refers to a higher retained enzyme activity over time as compared to other phytases.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein the term "gene" refers to a polynucleotide (e.g., a DNA segment), that encodes a polypeptide and includes regions preceding and following the coding regions as well as intervening sequences (introns) between individual coding segments (exons).

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In preferred embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "optimal alignment" refers to the alignment giving the highest percent identity score.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the invention are described by the following nomenclature: [original amino acid residue/position/substituted amino acid residue]. For example the substitution of glutamic acid (E) for arginine (R) at position 51 of SEQ ID NO:1 is represented as R51E. When more than one amino acid is substituted at a given position, the substitution is represented as 1) R51E, R51A, R51H or R51W; 2) R51E, A, H, or W or c) R51/E/A/H/W. When a position suitable for substitution is identified herein without a specific amino acid suggested, it is to be understood that any amino acid residue may be substituted for the amino acid residue present in the position. Where a variant phytase contains a deletion in comparison with other phytases the deletion is indicated with "*". For example, a deletion at position R51 is represented as R51*. A deletion of two or more consecutive amino acids is indicated for example as (51-54)*.

A "prosequence" is an amino acid sequence between the signal sequence and mature protein that is necessary for the secretion of the protein. Cleavage of the pro sequence will result in a mature active protein.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein.

"Host strain" or "host cell" refers to a suitable host for an expression vector comprising DNA according to the present invention.

The terms "derived from" and "obtained from" refer to not only a phytase produced or producible by a strain of the organism in question, but also a phytase encoded by a DNA sequence isolated from such strain and produced in a host organism containing such DNA sequence. Additionally, the term refers to a phytase which is encoded by a DNA sequence of synthetic and/or cDNA origin and which has the identifying characteristics of the phytase in question.

The term "isolated", "recovered" or "purified" refers to a material that is removed from its original environment.

A "feed" and a "food," respectively, means any natural or artificial diet, meal or the like or components of such meals intended or suitable for being eaten, taken in, digested, by an animal and a human being, respectively.

A "food or feed additive" is an essentially pure compound or a multi component composition intended for or suitable for being added to food or feed. It usually comprises one or more compounds such as vitamins, minerals or feed enhancing enzymes and suitable carriers and/or excipients, and it is usually provided in a form that is suitable for being added to animal feed.

The term "starch liquefaction" refers to a process by which starch is converted to shorter chain and less viscous dextrins.

The term "native *Buttiauxella* phytase (n-*Buttiauxella* phytase)" refers to a *Buttiauxella* phytase produced from the endogenous expression of the *Buttiauxella* phytase. For example, the term "n-*Buttiauxella* phytase" means the endogenous expression of a *Buttiauxella* phytase (i e, SEQ ID NO: 1) from a *Buttiauxella* species.

The terms "recombinant *Buttiauxella* phytase (r-*Buttiauxella* phytase)", "recombinantly expressed *Buttiauxella* phytase" and "recombinantly produced *Buttiauxella* phytase" refer to a mature *Buttiauxella* phytase protein sequence or variant that is produced in a host cell from the expression of a heterologous polynucleotide. For example, the term "r-*Buttiauxella* phytase" means the *Buttiauxella* phytase (i.e., SEQ ID NO: 1, 2 or 3) is expressed in a host in which a polynucleotide encoding the *Buttiauxella* phytase or a variant has been introduced.

A "promoter" is a regulatory sequence that is involved in binding RNA polymerase to initiate transcription of a gene.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein when describing proteins and genes that encode them, the term for the gene is italicized, (e.g., the gene that encodes *Buttiauxella* phytase). The term for the protein is generally not italicized and the first letter is generally capitalized.

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

Other definitions of terms may appear throughout the specification. Before the exemplary embodiments are described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Phytase Enzymes/Variants:

Phytase enzymes used as parent or precursor enzymes include a *Buttiauxella* sp. phytase and those enzymes corresponding to a *Buttiauxella* sp. phytase. In some embodiments, the parent *Buttiauxella* sp. phytase comprises the amino acid sequence of NCIMB (National Collections of Industrial Marine and Food Bacteria, Scotland, UK) accession number NCIMB 41248. In some embodiments, the parent *Buttiauxella* sp. phytase comprises the amino acid sequence of SEQ ID NO:1 or amino acid residues 34 to 446 of SEQ ID NO:1 (e.g., SEQ ID NO:2). In some embodiments, the parent *Buttiauxella* sp. phytase is derived from *B. agrestis, B. brennerase, B. ferragutiae, B. gaviniae, B. izardii, B. noackiae,* and *B. warmboldiae.* Reference is made to WO 2006/043178, which is specifically incorporated herein by reference and which describes phytases obtainable from or derived from a parent *Buttiauxella* sp. and phytases corresponding to a *Buttiauxella* sp. phytase enzyme. In some embodiments, a wild-type *Buttiauxella* sp phytase has at least 75%, at least 80%, at least 85%, at least 90%, at least 93%, at least 95%, at least 96%, at least 97%, at least 98%, and at least 99% amino acid sequence identity to the polypeptide of SEQ ID NO:1 or to the polypeptide of SEQ ID NO:2.

The present invention is concerned with variant phytases (e.g., variant *Buttiauxella* sp. phytases). Specifically, WO 2006/043178 describes the mutagenesis of a wild-type phytase enzyme having the sequence disclosed therein as SEQ ID NO:3 and referred to in the present application as SEQ ID NO:1 and SEQ ID NO:2. A number of preferred mutations are taught in WO 2006/043178. A variant phytase will contain at least one amino acid substitution, deletion or insertion, with amino acid substitutions being particularly preferred. The amino acid substitution, insertion or deletion may occur at any residue within the phytase peptide. A phytase variant of the present invention is a variant which does not have an amino acid sequence identical to the amino acid sequence of SEQ ID NO:2 herein.

In preferred embodiments of the present invention, the variant will comprise a substitution corresponding to positions A122, D125, T167, F197, T209, A211, K240, A242, S281, Q289, A294 and N303 in a *Buttiauxella* sp. phytase and more specifically corresponding to said equivalent positions in SEQ ID NO: 1. In some embodiments, the substitution comprises any of the remaining 19 amino acids corresponding to A, C, D, E, F, G, H, I, K, L, M, N, P, Q, R, S, T, V, W or Y. In some embodiments, the variant comprises the following amino acid substitutions A122T, D125A, T167I, F197S, T209K, A211P, K240E, A242S, S281L, Q289Y, A294E and N303K corresponding to SEQ ID NO:1.

In some embodiments, the phytase is a variant of the phytase designated BP-11, said BP-11 variant comprising amino acids residues 7-419 of SEQ ID NO:4. BP-11 is a variant of the BP-WT (SEQ ID NO:1 and SEQ ID NO:2).

In some embodiments, said variant of the BP-11 phytase comprises at least one substitution corresponding to positions R24, R28, T31, K32, D98, R100, K137, N212, G221, T225, E228, E249, H259, F263, M266, N276, H312, D313, T314, and/or D334 of SEQ ID NO: 4 or a sequence having at least 95%, at least 96%, at least 97%, at least 98% and at least 99% amino acid sequence identity inclusive of the variant substitutions of amino acid residues 7-419 of SEQ ID NO:4. In some embodiments, the variant will include more than one substitution, e.g. two, three, four or more substitutions. In another embodiment, the variant of BP-11 has a substitution at a position corresponding to D98. While the substitution may be any of the remaining 19 amino acids, in a preferred embodiment, the substitution is D98A. In further embodiments, the BP-11 variant having a substitution corresponding to position D98 will include one or more substitutions from the group corresponding to positions R24, R28, T31, K32, R100, K137, N212, G221, T225, E228, E249, H259, F263, M266, N276, H312, D313, T314, and/or D334 of SEQ ID NO:4. In some embodiments, the variant has the same or greater activity than the BP-11 phytase.

In a particularly preferred embodiment, the phytase variant comprises the polypeptide of SEQ ID NO:3. In another embodiment, the phytase variant consists of the polypeptide of SEQ ID NO:3.

In some embodiments, a variant according to the invention including an amino acid substitution in positions A122, D125, T167, F197, T209, A211, K240, A242, S281, Q289, A294 and N303 of SEQ ID NO:1 will further comprise a phytase having at least 90%, at least 92%, at least 93%, at least 94% and at least 95% sequence identity inclusive of the variant substitutions with amino acid residue 34-446 of the wild type phytase of SEQ ID NO:1.

In some embodiments, a variant according to the invention will include in addition to a substitution corresponding to positions A122, D125, T167, F197, T209, A211, K240, A242, S281, Q289, A294 and N303 in SEQ ID NO: 1, one or more substitutions corresponding to amino acid residues 59, 70, 193, 204, 221, 223, 225, 268, 336 and 351. In some embodiments, the variant will include the substitutions corresponding to K59E, N70Y, H193R, T204I, S221N, D223E, G225A, A268V, I336F and N351D of SEQ ID NO:1.

In some embodiments, a variant according to the invention will include a functional fragment. A functional fragment means a portion of the *Buttiauxella* spp. phytase that retains enzymatic function, preferably the fragment retains essentially the same amount of enzymatic function or a greater amount of enzymatic function as compared to the phytase polypeptide from which is was derived. In some embodiments, the variant which is a fragment will include a substitution corresponding to positions A122, D125, T167, F197, T209, A211, K240, A242, S281, Q289, A294 and N303 of SEQ ID NO:1 and at least 350, at least 375, or at least 400 amino acid residues of SEQ ID NO:1. In some embodiments, a variant according to the invention (e.g. SEQ ID NO:3) will be a fragment having at least 350, at least 375, or at least 400 amino acid residues.

Variants may be prepared by random mutagenesis, site saturation mutagenesis, and site specific mutagenesis of nucleotides in the DNA encoding the phytase protein, using cassette or PCR mutagenesis or other techniques well known in the art, to produce variants, which may thereafter be produced in cell culture. Reference is made to Morinaga et al., (1984) *Biotechnology* 2: 646-649; Nelson and Long, (1989) *Analytical Biochem.*, 180:147-151 and Sarkar and Sommer (1990) *Biotechniques* 8: 404-407. Variant phytase protein fragments may also be prepared by in vitro synthesis using established techniques.

Polynucleotides:

The present invention additionally encompasses polynucleotides which encode the variant phytases according to the invention. One skilled in the art is aware that, due to the degeneracy of the genetic code, nucleotide sequences may be produced in which the triplet codon usage, for some of the amino acids encoded by an original sequence has been changed thereby producing a different nucleotide sequence but one which encodes the same phytase as the original nucleotide sequence. For example a nucleotide sequence having a change in the third position on the triplet codon for all triplet codons would be about 66% identical to the original sequence, however, the amended nucleotide sequence would code the same phytase (e.g. having the same primary amino acid sequence).

Polynucleotides may be obtained by standard procedures known in the art from, for example, cloned DNA (e.g., a DNA "library"), by chemical synthesis, by cDNA cloning, by PCR (U.S. Pat. No. 4,683,202 or Saiki et al., (1988) 239:487-491), by synthetically established methods (Beucage et al., (1981) Tetrahedron Letters 22: 1859-1869 and Matthes et al, (1984) EMBO J. 3:801-895) or by the cloning of genomic DNA, or fragments thereof, substantially purified from a desired cell, such as a *Buttiauxella* sp. (See, for example, Sambrook et al., 2001, Molecular Cloning, A Laboratory Manual, 3d Ed., Cold Spring Harbor Laboratory Press, Cold Spring Harbor, N.Y.; Glover, D M and Hames, B D (Eds.), 1995, DNA Cloning 1: A Practical Approach and DNA Cloning 2: A Practical Approach, Oxford University Press, Oxford). Nucleic acid sequences derived from genomic DNA, and derivatives thereof, may contain regulatory regions in addition to coding regions.

TABLE 1

| Polynucleotide sequence of BP-WT |
|---|
| (SEQ ID NO: 5) |
| TTTCACATAGCAAACAACAACGAGACGAACTCGACGTTACCGCTTTGCTT |
| CTGGAGTATATTTATCAGACTCAAACACCCCAAAGAAAAGAGGCTGTAAA |
| TGACGATCTCTGCGTTTAACCGCAAAAAACTGACGCTTCACCCTGGTCTG |
| TTCGTAGCACTGAGCGCCATATTTTCATTAGGCTCTACGGCCTATGCCAA |
| CGACACTCCCGCTTCAGGCTACCAGGTTGAGAAAGTGGTAATACTCAGCC |
| GCCACGGGGTGCGAGCACCAACCAAAATGACACAGACCATGCGCGACGTA |
| ACACCTAATACCTGGCCCGAATGGCCAGTAAAATTGGGTTATATCACGCC |
| ACGCGGTGAGCATCTGATTAGCCTGATGGGCGGGTTTTATCGCCAGAAGT |
| TTCAACAACAGGGCATTTTATCGCAGGGCAGTTGCCCCACACCAAACTCA |
| ATTTATGTCTGGGCAGACGTTGATCAGCGCACGCTTAAAACTGGCGAAGC |
| TTTCCTGGCAGGGCTTGCTCCGGAATGTCATTTAACTATTCACCACCAGC |
| AGGACATCAAAAAAGCCGATCCGCTGTTCCATCCGGTGAAAGCGGGCACC |
| TGTTCAATGGATAAAACTCAGGTCCAACAGGCCGTTGAAAAAGAAGCTCA |
| AACCCCCATTGATAATCTGAATCAGCACTATATTCCCTTTCTGGCCTTGA |
| TGAATACGACCCTCAACTTTTCGACGTCGGCCTGGTGTCAGAAACACAGC |
| GCGGATAAAAGCTGTGATTTAGGGCTATCCATGCCGAGCAAGCTGTCGAT |

TABLE 1-continued

| Polynucleotide sequence of BP-WT |
|---|
| AAAAGATAATGGCAACAAAGTCGCTCTCGACGGGGCCATTGGCCTTTCGT |
| CTACGCTTGCTGAAATTTTCCTGCTGGAATATGCGCAAGGGATGCCGCAA |
| GCGGCGTGGGGGAATATTCATTCAGAGCAAGAGTGGGCGTCGCTACTGAA |
| ACTGCATAACGTCCAGTTTGATTTGATGGCACGCACGCCTTATATCGCCA |
| GACATAACGGCACGCCTTTATTGCAGGCCATCAGCAACGCGCTGAACCCG |
| AATGCCACCGAAAGCAAACTGCCTGATATCTCACCTGACAATAAGATCCT |
| GTTTATTGCCGGACACGATACCAATATTGCCAATATCGCAGGCATGCTCA |
| ACATGCGCTGGACGCTACCTGGGCAACCCGATAACACCCCTCCGGGCGGC |
| GCTTTAGTCTTTGAGCGTTTGGCCGATAAGTCAGGGAAACAATATGTTAG |
| CGTGAGCATGGTGTATCAGACTCTCGAGCAGTTGCGCTCCCAAACACCAC |
| TTAGCCTTAATCAACCTGCGGGAAGCGTACAGCTAAAAATTCCTGGCTGT |
| AACGATCAGACGGCTGAAGGATACTGCCCGCTGTCGACGTTCACTCGCGT |
| GGTTAGCCAAAGCGTGGAACCAGGCTGCCAGCTACAGTAAATATCAGACA |
| AAAAAAATGCCGCTCGCGATTAAGCGAACGGCATTACTTCCTAGCTTCCC |
| AGCTCGGATTAGCATGGCGAGAGCCGAAAAACTT |

It will be appreciated that the polynucleotide sequences provided in WO 2006/043178 (SEQ ID NO:1 and SEQ ID NO:2) will be useful for obtaining identical or homologous fragments of polynucleotides from other strains which encode enzymes having phytase activity. The polynucleotide sequence (SEQ ID NO:5) comprising the phytase gene from *Buttiauxella* P1-29 (BP-WT) is illustrated below in Table 1. The polynucleotide sequence (SEQ ID NO:14) comprising the phytase gene from the BP-17 variant is shown in Table 2 below.

TABLE 2

| Polynucleotide sequence of BP-17 |
|---|
| (SEQ ID NO: 14) |
| AACGACACCCCCGCCAGCGGCTACCAGGTCGAGAAGGTCGTCATCCTCAG |
| CCGCCACGGCGTCCGCGCCCCTACCAAGATGACCCAGACCATGCGCGACG |
| TCACCCCCAACACCTGGCCCGAGTGGCCCGTCAAGCTCGGCTACATCACC |
| CCTCGCGGCGAGCACCTCATCAGCCTCATGGGCGGCTTCTACCGCCAGAA |
| GTTCCAGCAGCAGGGCATCCTCAGCCAGGGCTCGTGCCCCACCCCCAACA |
| GCATCTACGTCTGGACTGACGTCGCCCAGCGCACCCTCAAGACCGGCGAG |
| GCCTTCCTCGCCGGCCTCGCCCCCCAGTGCGGCCTCACCATCCACCACCA |
| GCAGAACCTCGAGAAGGCCGACCCCCTCTTCCACCCCGTCAAGGCCGGCA |
| TCTGCAGCATGGACAAGACCCAGGTCCAGCAGGCCGTCGAGAAGGAGGCC |
| CAGACCCCCATCGACAACCTCAACCAGCACTACATCCCCAGCCTCGCCCT |
| CATGAACACCACCCTCAACTTCAGCAAGAGCCCCTGGTGCCAGAAGCACA |
| GCGCCGACAAGAGCTGCGACCTCGGCCTCAGCATGCCCAGCAAGCTCAGC |
| ATCAAGGACAACGGCAACGAGGTCTCCCTCGACGGCGCTATCGGCCTCAG |
| CTCCACCCTCGCCGAGATCTTCCTCCTCGAGTACGCCCAGGGCATGCCTC |

TABLE 2-continued

Polynucleotide sequence of BP-17

AGGCCGCCTGGGGCAACATCCACAGCGAGCAGGAGTGGGCCTCCTCCTC

AAGCTCCACAACGTCTACTTCGACCTCATGGAGCGCACCCCCTACATCGC

CCGCCACAAGGGCACCCCCCTCCTCCAGGCCATCAGCAACGCCCTCAACC

CCAACGCCACCGAGAGCAAGCTCCCCGACATCAGCCCCGACAACAAGATC

CTCTTCATCGCCGGCCACGACACCAACATCGCCAACATCGCCGGCATGCT

CAACATGCGCTGGACCCTCCCCGGCCAGCCCGACAACACCCCCCCTGGCG

GCGCTCTCGTCTTTGAGCGCCTCGCCGACAAGTCCGGCAAGCAGTACGTC

AGCGTCAGCATGGTCTACCAGACCCTCGAGCAGCTCCGCAGCCAGACCCC

CCTCAGCCTCAACCAGCCTGCCGGCAGCGTCCAGCTCAAGATCCCCGGCT

GCAACGACCAGACCGCCGAGGGCTACTGCCCCCTCAGCACCTTCACCCGC

GTCGTCAGCCAGAGCGTCGAGCCCGGCTGCCAGCTCCAGTAA

Properties:

In some embodiments, a variant phytase according to the invention will have altered properties. Preferably a variant according to the invention will have improved properties. In some embodiments, the altered, e.g., improved properties will be substrate specificity, catalytic activity, thermal stability, pH activity profile, specific activity and/or ability to release phosphate groups from phytate.

In some embodiments, a variant encompassed by the invention will have increased thermal stability as compared to a parent phytase (e.g., BP-WT or BP-11). In some embodiments, the variant will have a thermal stability difference (TD) of at least 1.5, at least 2.0, at least 2.5, at least 3.0, at least 5.0, at least 8.0, at least 10.0, at least 15.0, at least 18.0, and at least 20.0 compared to either BP-WT or BP-11.

In some embodiments, a variant encompassed by the invention (e.g. BP-17) will have an increase of thermostability of at least 3° C., at least 5° C., at least 10° C., at least 12° C., at least 15° C. and at least 20° C. at a pH of 4.5, 5.0, 5.5 or 6.0. More specifically, a variant of the invention (e.g. BP-17) will be thermostable at about 65° C., at about 70° C., at about 75° C., at about 80° C. or higher. In some embodiments, a phytase according to the invention is considered thermo stable if the enzyme retains greater than 50% of its activity after exposure to a specified temperature for 10 minutes at pH 5.5.

In some embodiments, a variant will have a higher proteolytic stability (residual activity). Proteolytic stability may be determined by the methods discloses in WO 2006/043178 and specific reference is made to Example 12 therein. In some embodiments, the variant encompassed by the invention will have residual activity of at least 45%, at least 50%, at least 55%, at least 60%, at least 65%, at least 70% and at least 85%.

In some embodiments, the phytase variant will have a specific activity greater than 100%, greater than 105%, greater than 110%, and also greater than 120% of a parent phytase or a thermostable variant thereof (e.g., BP-WT, SEQ ID NO:2 or BP-11) at a pH 4.0, at a pH 4.5, and at a pH 5.0. In some embodiments, the variant will have at least 5% at least 10%, at least 15%, at least 20%, and at least 25% higher specific activity as compared to the BP-11 phytase or the BP-WT (SEQ ID NO:2) phytase. In some embodiments, a variant encompassed by the invention will retain essentially the same level of thermostability as BP-WT or BP-11 but have an increase in specific activity under essentially the same conditions (e.g., pH).

In some embodiments, the variant phytase according to the invention will have a specific activity of at least 100 U/mg, at least 200 U/mg, at least 300 U/mg, at least 350 U/mg, at least 400 U/mg, at least 450 U/mg, at least 500 U/mg, at least 600 U/mg, at least 700 U/mg at least 800 U/mg at least 900 U/mg, at least 1000 U/mg and at least 1200 U/mg, wherein the specific activity is determined by incubating the phytase in a solution containing 2 mM phytase, 0.8 mMCaCl$_2$ in 200 mM sodium acetate buffer at pH 3.5 as detailed in example 1 of WO 2006/043178. In some embodiments, the specific activity is determined at an optimum pH 4.0.

In some embodiments, a variant phytase encompassed by the invention will have a specific activity ratio when compared to the phytase encoded by SEQ ID NO:5 of at least 110, at least 120 and at least 130.

In some embodiments, the pH activity maximum will be at least 0.1, at least 0.15, at least 0.2, at least 0.25, at least 0.3, at least 0.5, at least 0.6 at least 0.7, at least 0.8, and at least 1.0 pH units lower than the corresponding *Buttiauxella* sp phytase (e.g. SEQ ID NO:1 or SEQ ID NO:2) or at least 0.1, at least 0.15, at least 0.2, at least 0.25, at least 0.3, at least 0.5, at least 0.6 at least 0.7, at least 0.8, and at least 1.0 pH units lower than the BP-11 phytase. In some embodiments, a variant encompassed by the invention will have activity in the range of pH 2.0 to 6.0 and in some embodiments a maximum activity around pH 4.0 to pH 5.5 and also around pH 4.0 to pH 4.5.

In some embodiments, the variant encompassed by the invention may be used in a method of producing a phosphate compound comprising treating a phytate with a variant phytase encompassed by the invention (e.g., BP-17). The phytate may be myo-inositol di-, tri-, tetra, and/or pentaphosphates. Other suitable organic phosphates include inositol-tetraphosphates and inositol-oligophosphates.

Production of Phytase in Host Cells:

In some embodiments, the invention provides a method of producing an enzyme having phytase activity, comprising: (a) providing a host cell transformed with an expression vector comprising a polynucleotide encoding a variant phytase enzyme according to the invention said variant comprising at least one modification of at least one amino acid residue as described herein; (b) cultivating the transformed host cell under conditions suitable for the host cell to produce the phytase; and (c) recovering the phytase.

In some embodiments, the expression vector will comprise a polynucleotide which encodes a phytase comprising an amino acid sequence having a substitution in amino acid residues corresponding to positions A122, D125, T167, F197, T209, A211, K240, A242, S281, Q289, A294 and N303 of SEQ ID NO:1 and in other embodiments, the substitution corresponds to A122T, D125A, T167I, F197S, T209K, A211P, K240E, A242S, S281L, Q289Y, A294E and N303K of SEQ ID NO:1. In some embodiments, the expression vector comprises a polynucleotide which encodes a variant phytase comprising a substitution corresponding to positions R24, R28, T31, K32, D98, R100, K137, N212, G221, T225, E228, E249, H259, F263, M266, N276, H312, D313, T314, and/or D334 of SEQ ID NO: 4. In other embodiments, the vector includes a polynucleotide encoding a phytase comprising SEQ ID NO:3.

In some embodiments of the invention, the host strain is genetically engineered to express heterologous phytases or variants having phytase activity according to the invention herein.

Host Cells

Host cells useful for the production of a phytase encompassed by the invention include bacterial cells, fungal cells and plant cells. Host cells include both the cells and progeny of the cells and protoplasts created from the cells which may be used to produce a variant phytase according to the invention.

In some embodiments, the host cells are fungal cells and preferably filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. The filamentous fungal parent cell may be a cell including, but not limited to, *Trichoderma* sp., (e.g., *Trichoderma reesei*, the asexual morph of *Hypocrea jecorina*, previously classified as *T. longibrachiatum, Trichoderma viride, Trichoderma koningii, Trichoderma harzianum*); *Penicillium* sp., *Humicola* sp. (e.g., *H. insolens, H. lanuginosa* and *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans,* and *A. awamori*), *Fusarium* sp., (e.g. *F. roseum, F. graminum F. cerealis, F. oxysporuim* and *F. venenatum*), *Neurospora* sp., (*N. crassa*), *Hypocrea* sp., *Mucor* sp., (*M. miehei*), *Rhizopus* sp. and *Emericella* sp. (See also, Innis et al., (1985) *Sci.* 228:21-26). *Aspergillus* strains useful for expression of the phytases (and/or alpha amylases) of the invention are disclosed in e.g., Ward et al. (1993) *Appl. Microbiol. Biotechnol.* 39:738-743 and Goedegebuur et al., (2002) *Curr Gene* 41:89-98. In some embodiments, the host is a strain of *Trichoderma*, and particularly a strain of *T. reesei*. Strains of *T. reesei* are known and non-limiting examples include e.g., ATCC No. 13631, ATCC No. 26921, ATCC No. 56764, ATCC No. 56765, ATCC No. 56767 and NRRL 15709. In some embodiments, the host strain is a derivative of RL-P37. RL-P37 is disclosed in Sheir-Neiss et al. (1984) *Appl. Microbiol. Biotechnology* 20:46-53.

In some embodiments, the host cells will be gram-positive bacterial cells. Non-limiting examples include strains of *Streptomyces*, (e.g., *S. lividans, S. coelicolor* and *S. griseus*) and *Bacillus*. As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis.*

In some embodiments the host cell is a gram-negative bacterial strain, such as *E. coli* or *Pseudomonas* sp.

In other embodiments, the host cells may be yeast cells such as *Saccharomyces, Schizosaccharomyces* sp, *Pichia* sp., or *Candida* sp.

In some embodiments, the host strain may have been previously manipulated through genetic engineering. In some embodiments, various native genes of the fungal host cell will have been inactivated. These genes include, for example genes encoding cellulolytic enzymes, such as endoglucanases (EG) and exocellobiohydrolases (CBH) (e.g. cbh1, cbh2, egl1, egl2 and egl3). For example, U.S. Pat. No. 5,650,322 discloses derivative strains of RL-P37 having deletions in the cbh1 gene and the cbh2 gene. (See, e.g., U.S. Pat. No. 5,847,276 and WO 05/001036).

In other embodiments, the host cell may be a plant cell and the invention is applicable to both dicotyledonous plants (e.g., tomato, potato, soybean, cotton, and tobacco) and monocotyledonous plants, including, but not limited to graminaceous monocots such as wheat (*Triticum* spp.), rice (*Oryza* spp.), barley (*Hordeum* spp.), oat (*Avena* spp.), rye (*Secale* spp.), corn (*Zea mays*), sorghum (*Sorghum* spp.) and millet (*Pennisetum* spp).

Vectors

Useful vectors including DNA constructs comprising a polynucleotide encoding a phytase of the invention and transformation methods of host cells are well known in the art and standard techniques and methodology may be used.

According to the invention, a DNA construct comprising nucleic acid encoding a variant phytase encompassed by the invention is constructed to transfer and/or express the variant in a host cell. In one embodiment, the DNA construct is transferred to a host cell by an expression vector which comprises regulatory sequences (e.g. promoters, ribosomal binding sites, transcriptional start and stop sequences, translational start and stop sequences, enhancers, activator sequences, cell specific expression sequences, signal sequences, and/or terminators) operably linked to the variant phytase coding sequence.

An expression vector comprising a DNA construct with a polynucleotide encoding variant phytase can be any vector which is capable of replicating autonomously in a given fungal host organism or of integrating into the DNA of the host. In some embodiments, the expression vector is a plasmid or a bacteriophage. In some embodiments, the expression vector is preassembled and contains sequences required for high-level transcription and a selectable marker. In some embodiments, the coding region for variant phytase gene or part thereof is inserted into this general-purpose expression vector such that it is under the transcriptional control of the expression construct promoter and terminator sequences. In some embodiments, genes or part thereof are inserted downstream of the strong cbh1 promoter.

Briefly with respect to production of a phytase in fungal host cells reference in made to Sambrook et al., (1989) supra, Ausubel (1987) supra, van den Hondel et al. (1991) in Bennett and Lasure (Eds.) MORE GENE MANIPULATIONS IN FUNGI, Academic Press (1991) pp. 70-76 and 396-428; Nunberg et al., (1984) *Mol. Cell. Biol.* 4:2306-2315; Boel et al., (1984) *EMBO J.* 3:1581-1585; Finkelstein in BIOTECHNOLOGY OF FILAMENTOUS FUNGI, Finkelstein et al. Eds. Butterworth-Heinemann, Boston, Mass. (1992), Chap. 6; Kinghorn et al. (1992) APPLIED MOLECULAR GENETICS OF FILAMENTOUS FUNGI, Blackie Academic and Professional, Chapman and Hall, London; Kelley et al., (1985) EMBO J. 4:475-479; Penttila et al., (1987) Gene 61:155-164; and U.S. Pat. No. 5,874,276. A list of suitable vectors may be found on the website of the Fungal Genetics Stock Center Catalogue of Strains (FGSC). Suitable vectors include those obtained from for example Invitrogen Life Technologies and Promega. Specific vectors suitable for use in fungal host cells include vectors such as pFB6, pBR322, pUC18, pUC100, pDON™201, pDONR™221, pEN-TRTR™, pGEM®3Z and pGEM®4Z.

In some embodiments, the vector can be any vector which, when introduced into a fungal host cell, is integrated into the host cell genome and is replicated. Some non-limiting examples of such vectors is provided on the website of the Fungal Genetics Stock Center Catalogue of Strains (FGSC). Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pTREX, pFB6, pBR322, PUC18, pUC100 and pENTR/D. Suitable plasmids for use in bacterial cells include pBR322 and pUC19 permitting replication in E. coli and pE194 for example permitting replication in Bacillus.

In some embodiments, nucleic acids encoding variant phytase encompassed by the invention are operably linked to a suitable promoter, which shows transcriptional activity in the host cell. In general, the expression of the variant phytase is accomplished under any suitable promoter known or later discovered in the art. In some embodiments, the variant phytase is expressed under a promoter native to the host. In some embodiments, the phytase variant is expressed under a heterologous promoter that is active in the host cell. For example, if a Trichoderma cell is used as the host cell, preferably, the promoter is active in a Trichoderma host cell.

In some embodiments, the promoter is a constitutive or inducible promoter. A "constitutive promoter" is a promoter that is active under most environmental and developmental conditions. An "inducible" or "repressible" promoter is a promoter that is active under environmental or developmental regulation. In some embodiments, promoters are inducible or repressible due to changes in environmental factors including but not limited to, carbon, nitrogen or other nutrient availability, temperature, pH, osmolarity, the presence of heavy metal(s), the concentration of inhibitor(s), stress, or a combination of the foregoing, as is known in the art. In some embodiments, the inducible or repressible promoters are inducible or repressible by metabolic factors, such as the level of certain carbon sources, the level of certain energy sources, the level of certain catabolites, or a combination of the foregoing as is known in the art. In one embodiment, the promoter is one that is native to the host cell. For example, when T. reesei is the host, the promoter is a native T. reesei promoter such as the cbh1 promoter which is deposited in GenBank under Accession Number D86235.

Suitable non-limiting examples of promoters include cbh1, cbh2, egl1, egl2, egl3, egl4, egl5, xyn1, and xyn2, respressible acid phosphatase gene (phoA) promoter of P. chrysogenus (See e.g., Graessle et al., (1997) *Appl. Environ. Microbiol.,* 63:753-756), glucose repressible PCK1 promoter (See e.g., Leuker et al., (1997), *Gene,* 192:235-240), maltose-inducible, glucose-repressible MET3 promoter (See Liu et al., (2006), *Eukary. Cell,* 5:638-649), pKi promoter and cpc1 promoter. Other examples of useful promoters include promoters from *A. awamori* and *A. niger* glucoamylase genes (see e.g., Nunberg et al., (1984) *Mol. Cell. Biol.* 4:2306-2315 and Boel et al., (1984) *EMBO J.* 3:1581-1585). Also, the promoters of the *T. reesei* xln1 gene may be useful (see e.g., EPA 137280A1).

In some embodiments, the promoter is a temperature-sensitive promoter. Preferably, the activity of the temperature-sensitive promoter is repressed by elevated temperature. In some embodiments, the promoter is a catabolite-repressed promoter or a promoter repressed by changes in osmolarity. In some embodiments, the promoter is inducible or repressible by the levels of polysaccharides, disaccharides, or monosaccharides present in the culture medium.

In some embodiments, the variant phytase coding sequence is operably linked to a signal sequence. The signal sequence is not critical to the invention, but can be any signal sequence that is active as a signal sequence in the host cell. The DNA encoding the signal sequence can be that which is naturally associated with the host cell, promoter, or phytase. In some embodiments, the signal sequence is naturally associated with the variant phytase gene to be expressed. In additional embodiments, a signal sequence and a promoter sequence comprising a DNA construct or vector to be introduced into a fungal host cell are derived from the same source. For example, in some embodiments, the signal sequence is the cbh1 signal sequence which is operably linked to a cbh1 promoter.

In some embodiments, the expression vector also includes a transcription termination sequence downstream of the structural gene to provide for efficient termination. In some embodiments, the termination sequence and the promoter sequence are derived from the same source. In other embodiments, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (see e.g., Nunberg et al. (1984) supra, and Boel et al., (1984) supra).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS argB and pyr4. Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6; and Kinghorn et al. (1992) APPLIED MOLECULAR GENETICS OF FILAMENTOUS FUNGI, Blackie Academic and Professional, Chapman and Hall, London). In some embodiments, the selective marker is the amdS gene, which encodes the enzyme acetamidase, allowing transformed cells to grow on acetamide as a nitrogen source. The use of *A. nidulans* amdS gene as a selective marker is described in, for example, Kelley et al., (1985) *EMBO J.* 4:475-479 and Penttila et al., (1987) *Gene* 61:155-164.

Methods used to ligate the DNA construct comprising a polynucleotide encoding the phytase variant, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, e.g., Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Transformation, Expression and Culture of Host Cells

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion.

Transformation methods for *Aspergillus* and *Trichoderma* are described in, for example, Yelton et al (1984) Proc. Natl. Acad. Sci. USA 81:1470-1474; Berka et al., (1991) in Applications of Enzyme Biotechnology, Eds. Kelly and Baldwin, Plenum Press (NY); Cao et al., (2000) *Sci.* 9:991-1001; Campbell et al., (1989) *Curr. Genet.* 16:53-56; Pentilla et al., (1987) *Gene* 61:155-164); de Groot et al., (1998) *Nat. Biotechnol.* 16:839-842; U.S. Pat. No. 6,022,725; U.S. Pat. No. 6,268,328 and EP 238 023. The expression of heterologous protein in *Trichoderma* is described in U.S. Pat. No. 6,022, 725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous*

*Genes*", in MOLECULAR INDUSTRIAL MYCOLOGY, Eds. Leong and Berka, Marcel Dekker Inc., NY (1992) pp. 129-148). Reference is also made to WO96/00787 and Bajar et al., (1991) Proc. Natl. Acad. Sci. USA 88:8202-28212 for transformation of *Fusarium* strains.

Methods for making DNA constructs useful in transformation of plants and methods for plant transformation are also known. Some of these methods include *Agrobacterium tumefaciens* mediated gene transfer; microprojectile bombardment, PEG mediated transformation of protoplasts, electroporation and the like. Reference is made to, for example, U.S. Pat. No. 5,780,708; U.S. Pat. No. 6,803,499; U.S. Pat. No. 6,777,589; Fromm et al (1990) *Biotechnol.* 8:833-839; Potrykus et al (1985) *Mol. Gen. Genet.* 199:169-177; Brisson et al., (1984) Nature 310:511-514; Takamatsu et al., (1987) EMBO J. 6:307-311; Coruzzi et al., (1984) EMBO J. 3:1671-1680; Broglie et al (1984) Science 224:838-843; Winter J and Sinibaldi R M (1991) Results Probl Cell Differ 17:85-105; Hobbs S or Murry L E (1992) in McGraw Hill Yearbook of Science and Technology, McGraw Hill, New York, N.Y., pp 191-196; and Weissbach and Weissbach (1988) Methods for Plant Molecular Biology, Academic Press, New York, N.Y., pp 421-463. Transformed cells may be cultured using standard techniques under suitable conditions in shake flask cultivation, small scale or large scale fermentations (including continuous, batch and fed batch fermentations) in laboratory or industrial fermentors, with suitable medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) find use in the present invention. Preferred culture conditions for filamentous fungal cells are known in the art and may be found in the scientific literature and/or from the source of the fungi such as the American Type Culture Collection and Fungal Genetics Stock Center.

In some embodiments, genetically stable transformants are constructed with vector systems whereby the nucleic acid encoding a phytase variant is stably integrated into a host strain chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium. After fungal growth has been established, transformed cells are exposed to conditions effective to cause or permit the expression of phytase variants as defined herein. In cases where the phytase variant coding sequence is under the control of an inducible promoter, the inducing agent (e.g., a sugar, metal salt or antimicrobial), is added to the medium at a concentration effective to induce expression.

Assays for Phytase Expression/Activity

In order to evaluate the expression of phytase variants having phytase activity by a cell line that has been transformed with a heterologous polynucleotide encoding a phytase variant having phytase activity encompassed by the invention, assays can be carried out at the protein level, the RNA level or by use of functional bioassays particular to phytase activity and/or production. In general assays employed include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a phytase variant having phytase activity may be measured in a sample directly, for example, by assays directly measuring phytase Activity (FTU) by the release of inorganic phosphate. The inorganic phosphate forms a yellow complex with acidic molybdate/vandate reagent and the yellow complex was measured at a wavelength of 415 nm in a spectrophometer and the released inorganic phosphate was quantified with a phosphate standard curve. One unit of phytase (FTU) is the amount of enzyme that releases 1 micromole of inorganic phosphate from phytate per minute under the reaction conditions given in the European Standard (CEN/TC 327,2005-TC327WI 003270XX).

In addition, gene expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a phytase. The details of such methods are known to those of skill in the art and many reagents for practicing such methods are commercially available.

Assays for phytase activity are well known in the art and one example is the classic assay for liberation of inorganic phosphate developed by Fiske and SubbaRow, *Journal of Biological Chemistry* 66:375-392 (1925). A variation of this method is found in Mitchell et al., *Microbiol.* 143:245-252 (1997). An alternative method is described in FOOD CHEMICALS CODEX, 4th Edition, Committee on Food Chemicals Codex, Institute of Medicine, National Academy Press, Washington, D.C., 1996 at pages 809-810. Each of these references is incorporated herein. In a number of these assays colorimetry is then performed using a spectrophotometer and compared to controls of known concentration of inorganic phosphate ($P_i$) and/or controls produced by reactions with enzymes having known phytase activity. A Unit of activity is determined as the amount of enzyme sample required to liberate 1 μmol $P_i$ per minute from phytate under defined reaction conditions. Reference is also made to U.S. Pat. No. 6,221,644 and U.S. Pat. No. 6,139,902.

In some embodiments of the invention, the phytase variants having phytase activity expressed by a *Trichoderma* or *Aspergillus* host will be greater than 1 gram protein per liter (g/L), greater than 2 g/L, greater than 5 g/L, greater than 10 g/L, greater than 20 g/L, greater than 25 g/L, greater than 30 g/L, greater than 50 g/L and also greater than 100 g/L of culture media.

Protein Recovery

The polypeptides produced upon expression of the nucleic acid sequences of this invention can be recovered or isolated from the fermentation of cell cultures and substantially purified in a variety of ways according to well established techniques in the art. One of skill in the art is capable of selecting the most appropriate isolation and purification techniques. The phytase of the invention can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, METHODS IN ENZYMOLOGY, 182 (1990); Scopes, PROTEIN PURIFICATION: PRINCIPLES AND PRACTICE, Springer-Verlag, New York (1982). The purification step(s) selected will depend, for example, on the nature of the production process used and the particular form of phytase produced.

In general, a phytase variant (including n-*Buttiauxella* phytase or r-*Buttiauxella* phytase) produced in cell culture is secreted into the medium and may be purified or isolated, e.g., by removing unwanted components from the cell culture medium. In some cases, the phytase variant can be produced in a cellular form necessitating recovery from a cell lysate. In such cases the enzyme is purified from the cells in which it was produced using techniques routinely employed by those of skill in the art. Examples include, but are not limited to, affinity chromatography (see e.g., Tilbeurgh et al., (1984) *FEBS Lett.* 16:215); ion-exchange chromatographic methods (see e.g. Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (see e.g., Medve et al., (1998) *J. Chromatography A* 808:153); hydrophobic interaction chromatography (see e.g., Tomaz and Queiroz, (1999) *J. Chromatography A* 865:123); two-phase partitioning (see e.g., Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; and/or gel filtration using, e.g., Sephadex G-75.

Fermentations

In some embodiments of the present invention, fungal cells expressing a heterologous phytase variants are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Applications and Methods of Use

In an embodiment of the invention, an enzyme composition is provided comprising at least one phytase in accordance with the invention. Compositions according to the invention may be prepared in accordance with methods known in the art and may be in the form of a liquid or a dry composition.

Liquid compositions need not contain anything more than the phytase enzyme, which may be in either a substantially purified or unpurified form, preferably in a substantially purified form. Usually, however, a stabilizer such as glycerol, sorbitol or mono propylene glycol is also added. The liquid composition may also comprise one or more other additives, such as salts, sugars, preservatives, pH-adjusting agents (i.e., buffering agents), proteins, or phytate (a phytase substrate). Typical liquid compositions are aqueous or oil-based slurries.

Dry compositions may be spray-dried compositions, in which case the composition need not contain anything more than the enzyme in a dry form. Usually, however, dry compositions are so-called granulates which may readily be mixed with for example food or feed components, or more preferably, form a component of a pre-mix. The particle size of the enzyme granulates preferably is compatible with that of the other components of the mixture.

In some embodiments, an enzyme composition including a variant phytase encompassed by the invention will be optionally used in combination with any one or combination of the following enzymes—glucoamylases, alpha amylases, proteases, pullulanases, isoamylases, cellulases, hemicellulases, xylanases, cyclodextrin glycotransferases, lipases, phytases, laccases, oxidases, esterases, cutinases, other phytases and combinations thereof.

In some embodiments, the phytase composition is a food or animal feed composition. A food or animal feed composition may comprise a phytase at a concentration of 10 to 15,000 U/kg feed or food (e.g. 100 to 5,000 U/kg, 200-2,000 U/kg and also 500-1000 U kg/). The phytase composition may be used as an additive which is active in the digestive tract, of livestock, such as poultry and swine, and aquatic farm animals including fish and shrimp. The present invention contemplates a method for the production of a food or animal feed, characterized in that phytase according to the invention is mixed with said food or animal feed. The liquid compositions can be added to a food or feed after an optional pelleting thereof.

In some embodiments, the animal feed will comprise one or more of the following components: a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins; f) supplements, such as enzymes, betaine, flavors, essential oils, antibiotic growth promoters, coccidiostats, probiotics, and prebiotics.

Also provided is a method for the reduction of levels of phosphorus in animal manure, characterized in that an animal is fed an animal feed according to the invention in an amount effective in converting phytate contained in said animal feed.

Further the phytase compositions encompassed by the invention may be used in method of starch hydrolysis. The phytase composition may be added during a starch liquefaction step, a saccharification step and/or during a fermentation step. Alpha-amylases are used to break down starch 1-4 linkages during industrial starch hydrolysis processes using reduced plant material such as milled grains as a feedstock (e.g. in brewing, and baking). Amylases are required to break down starch and obtaining adequate activity of these enzymes is sometimes problematic. It has been known for some time that phytate has an inhibitory effect on amylases. Therefore enzyme compositions comprising a phytase according to the invention may be used in starch hydrolysis process to reduce the inhibitory effect of phytate on alpha amylase (EP 0 813607B).

Phytases, phytate and lower phosphate phytate derivatives find many other uses in personal care products, medical products and food and nutritional products, as well as various industrial applications, particularly in the cleaning, textile, lithographic and chemical arts.

The following examples are offered for illustrative purposes only, and are not intended to limit the scope of the present invention in any way.

EXPERIMENTAL

Abbreviations

In the disclosure and experimental section which follows, the following abbreviations apply: ° C. (degrees Centigrade); rpm (revolutions per minute); $H_2O$ (water); $dH_2O$ (deionized water); $dIH_2O$ (deionized water, Milli-Q filtration); aa or AA (amino acid); bp (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec(s) or s(s) (second/seconds); min(s) or m(s) (minute/minutes); hr(s) or h(s) (hour/hours); AMM solution (7.5N $H_2SO_4$, 15 mM ammonium molybdate and acetone (1:1:2)); ABS (Absorbance); EtOH (ethanol); PPS (physiological salt solution; m/v (mass/volume); and MTP (microtiter plate).

The following assays and methods are used in the examples provided below:

The methods used to provide variants are described below. However, it should be noted that different methods may be used to provide variants of a parent molecule and the invention is not limited to the methods used in the examples. It is intended that any suitable means for making variants and selection of variants may be used.

*Buttiauxella* sp strain P1-29 was deposited with NCIMB under accession No: 41248. The isolation of this strain from plant material and the taxonomic identification are described in WO 2006/043178 (See, Examples 1-4). In addition, the cloning of chromosomal DNA, amplification and expression of the phytase gene from *Buttiauxella* sp. strain P1-29 in *E. coli* is also described (See, Examples 5-6). The *Buttiauxella* sp. strain P1-29 phytase described in WO 2006/043178 is also referred to herein as BP-WT and reference is made to SEQ ID NO:1 and SEQ ID NO:2 herein.

Phytase Enzymatic Activity Assay

These assays were carried out in 2 buffer systems. For pH 4.0 to 5.5 sodium acetate buffers were used. These were prepared by titrating 250 mM sodium acetate with HCL to the indicated pH value. The buffers for pH 2.0 to 3.5 were prepared by titration of 250 mM Glycine with HCL to the indicated pH value. The assay at pH 4.0 was used as a standard. In addition to buffer, the reaction mixture contained 6 mM phytate and 1.0 mM $CaCl_2$ and 0.05 mg/ml BSA. Reactions were allowed to proceed for 1 hr at 37° C. The release of phosphate was measured using a molybdate assay, such as disclosed in Heinonen et al. (Heinonen, J. K., Lahti, R. J., Anal Biochem. 113(2), 313-317 91981)). Briefly, 200 µl of a freshly prepared AMM solution was added to 100 µl reaction mixture in each microtiter plate well. The absorbance at 390 nm was measured not earlier than 10 min and not later than 30 min after addition of AMM reagent. The amount of phosphate was determined by building a calibration curve with phosphate solution of known concentrations. The specific absorption values (A280) of phytase variants were calculated on the basis of amino acid composition of the protein using Vector NTI software (Invitrogen).

Specific Activity Assay

Phytase activity was determined in microtiter plates using a coupled enzymatic assay: Enzyme preparations were diluted in dilution buffer (50 mM sodium acetate, 0.05% Pluronic F-68, 1 mg/ml BSA). To 5 µl of the enzymatic solution 75 µl of the phytase assay mixture (500 mM Glycine/HCl, pH 4.0, 10.67 mM phytate, 1 mM $CaCl_2$, 0.05% (w/v) Pluronic F-68) were added. The assay was incubated 1 h at 37° C. Then 10 µl of the assay were mixed with 40 µl of the detection assay mixture (1M Tris/HCl, pH 7.0, 0.01% (v/v) Triton X-100, 25 µM ADHP (MoBiTec, Göttingen, Germany), 0.25 u/ml maltosephosphorylase, 0.3125 mM maltose, 1.5625 u/ml glucose oxidase, 0.3125 u/ml horseradish peroxidase, 1 mM EDTA, 0.35 mg/ml BSA) and incubated for 1 h at 37° C. The reaction was stopped by the addition of 30 µl of 2700 u/ml catalase in $H_2O$. Fluorescence at 595 nm was then measured, using 535 nm as excitation wavelength. The amount of phosphate was determined using a calibration curve with phosphate solutions of known concentrations.

Protein determination was done by absorption measurement at A280 nm. The specific absorption values (A280) of phytase variants were calculated on the basis of amino acid compositions of the protein using the method of Gill and von Hippel (Anal. Biochem. 182:319-326 (1989)).

Thermostability

The thermostability of variants was characterized by the inactivation temperature of the enzyme. The inactivation temperature was determined by measuring the residual activity of the phytase enzyme after incubation for 10 min at different temperatures and subsequent cooling to room temperature. The inactivation temperature is the temperature at which the residual activity is 50% compared to the residual activity after incubation for the same duration under the same conditions at room temperature. In order to determine the temperature corresponding to 50% residual activity, interpolations and extrapolations from the measured activity data were computed, where appropriate. Thermostability differences in ° C. were calculated by subtracting the inactivation temperatures of two enzymes from each other.

Purification of the BP-11 Mutants

Purification was performed by cultivating *Bacillus subtilis*, transformed with a plasmid coding for BP-11, in shake flasks at 37° C. and 160 rpm using standard LB medium with addition of 20 mg/l Neomycin. At this stage, the culture medium accumulated significant amount of phytase activity. About 2 L of the culture broth were adjusted to pH 8.0, filtered and applied to a column packed with 10 ml of Ni-NTA sepharose resin (Qiagen). The column was washed with 50 mM Tris-HCl buffer, 300 mM NaCl, pH 8.0 until OD280 dropped below 0.05. Subsequently the bound phytase was eluted with the same buffer containing 250 mM imidazole hydrochloride. The elutate was dialyzed against 50 mM sodium acetate buffer pH 5.0 and stored at 4° C. The enzyme solution was then applied to a Resource S column equilibrated with 20 mM sodium acetate buffer pH 5.0 and the elution was performed using a salt gradient from 0-1M NaCl over 10 column volumes. Optionally the eluate was dialyzed against 20 mM sodium acetate buffer pH 5.0 before storing at 4° C.

Pepsin Stability

The pepsin stability of such variants was characterized by residual activities measured at pH 3.5, 37° C. after pepsin incubation compared to control conditions (residual activity=activity after pepsin incubation/activity after incubation under control conditions). The pepsin incubation was performed for 2 hours at pH 2.0, 0.25 mg/ml pepsin, 1 mM $CaCl_2$ and 5 mg/ml BSA at 37° C. Control conditions were 2 hours at pH 5.0, 1 mM $CaCl_2$ and 5 mg/ml BSA at 37° C.

In the examples that follow, amino acid residues in the sequence of phytase variants are numbered according to the sequence of the BP-WT (SEQ ID NO:1) unless otherwise noted.

Example 1

Generation and Characterization of Phytase Variants

In general, phytase variants were constructed by mutagenesis of the nucleotide sequence SEQ ID NO:5 using mutagenesis methods such as those methods disclosed in Morinaga et al (Biotechnology (1984) 2, p 646-649); in Nelson and Long (Analytical Biochemistry (1989), 180, p 147-151); or the Error Threshold Mutagenesis protocol described in WO 92/18645. Another suitable method for mutagenic PCR is disclosed by Cadwell and Joyce (PCR Methods Appl. 3 (1994), 136-140).

Phytase enzyme variants were characterized after heterologous expression in one or more of the following expression hosts: *Escherichia coli* K12; *Bacillus subtilis*; *Saccharomyces cerevisiae*. Phytase variants were derived which differed in one or more amino acid positions from SEQ ID NO:1, including two positions, three positions, four positions, five positions, six positions, seven positions, eight positions, nine positions, ten positions, eleven positions, twelve positions. Where appropriate iterative rounds of mutagenesis, were performed. Following the protocols described in WO 2006/043178 various mutations were observed in the BP-WT. In particular one mutant, A122T/D125A/T1671/F197S/T209K/A211P/K240E/A242S/S281L/Q289Y/A294E/N303K designated BP-11 having increased thermostability over BP-WT was observed (See, amino acid residue 7-419 of SEQ ID NO:4 which corresponds to SEQ ID NO:6).

Example 2

Variants of BP-11

Three different strategies were used to obtain variants of BP-11 which included random mutagenesis, directed mutagenesis and site saturation mutagenesis.

A. Random mutagenesis and high throughput screening were performed according to the teachings described in WO 2006/043078 for obtaining BP-WT mutants, such as BP-11.

One specific variant of BP-1 obtained by this method was designated BP-19. BP-19 differs from BP-11 by a substitution at position 54 (Y54H), 84 (S84G), 190 (S190G), 220 (I220V) and 289 (N289D) corresponding to SEQ ID NO: 4. Using the assay as described above to measure specific activity, it was determined that BP-19 has a specific activity at pH 4.0 that was higher 26% higher than BP-11 and reference is made to Table 3.

B. Directed mutagenesis of three specific residues was performed on the BP-WT backbone and the BP-11 backbone which corresponds to positions G221S, T225M and N276R of SEQ ID NO:4. The mutant BP-15 was obtained from the BP-WT backbone and the mutant BP-16 was obtained from the BP-11 backbone. The specific activity relative to the parent phytases is described in Table 3.

C. Site-saturation mutagenesis libraries based on the variant BP-11 molecule at various positions was performed. The positions included R24, R28, T31, K32, D98, R100, K137, N212, G221, T225, E228, H259, F263, M266, N276, H312, D313, T314, and D334 of SEQ ID NO:4. The libraries were initially screened for improved activity in a high throughput screen and then some variants were screened for specific activity as described above. Selected variant were further purified to about 97% purity and analyzed for specific activity. Two variants at position D98 yielded improved specific activity (D98A and D98Q). The mutant having ala (A) instead of asp (D) (D98A) was isolated and designated as BP-17 (See, SEQ ID NO: 3). The mutant having gln (Q) instead of asp (D) (D98Q) was isolated and designated as BP-20.

The variants of BP-11, which include BP-16, BP-17, BP-18, BP-19 and BP-20 were all tested as described above for phytase activity.

TABLE 3

Specific activity (U/mg, pH 4.0, 97% enzyme purity)

| VARIANT | Specific Activity (U/mg) | Specific Activity (% of BP-WT activity) | Specific Activity (% of BP-11 activity) |
|---|---|---|---|
| BP-WT (P1-29) | 936 | 100 | 142 |
| BP-11 | 632 | 70 | 100 |
| BP-15 | 790 | 85 | 121 |
| BP-16 | 760 | 74 | 106 |
| BP-17 | 1017 | 109 | 156 |
| BP-18 | 1005 | 107 | 153 |
| BP-19 | 822 | 88 | 126 |
| BP-20 | 840 | 93 | 133 |

Example 3

Expression of BP-17 in *E. coli*

The DNA sequence of the BP-17 mutant was modified for expression in *E. coli* by including DNA sequences that encode the signal sequence of the wild-type *Buttiauxella* phytase followed by "6×His tag" and the coding sequence corresponding to the mature *Buttiauxella* phytase mutant BP17. Using standard genetic engineering methods this nucleotide sequence was inserted between the promoter of the *E. coli* dps gene and transcription terminator of the tufA gene, also derived from *E. coli*.

The expression cassette was inserted between SacI and ApaI restriction sites of the *E. coli* vector pCR 2.1. (Invitrogen) resulting in plasmid pCDP(SHOK). The structure of the expression vector pCDP(SHOK) is illustrated by FIG. 2.

*E. coli* strain XL-Blue MRF' transformed with pCDP (SHOK) was cultivated in shake flasks at 37° C. and 200 rpm using standard LB medium with addition of 50 mg/l of kanamycin. At this stage, the culture medium accumulated a significant amount of phytase activity which was not detectable in the recipient strain transformed with pCR2.1 and cultivated on the same medium. About 2 l of this culture broth was adjusted to pH 8.0 and applied to a column packed with 25 ml of Ni-NTA agarose (Invitrogen). The column was washed with 20 mM Tris-HCl buffer, pH 8.0 until $OD_{280}$ dropped below 0.05 followed by elution of the bound phytase with the same buffer containing 200 mM imidazole hydrochloride. The elutate was dialysed against 20 mM sodium acetate buffer, pH 5.5 and stored at either 4° C. or frozen at −20° C. No loss of activity was observed upon repeated freezing-thawing.

Figure 3:
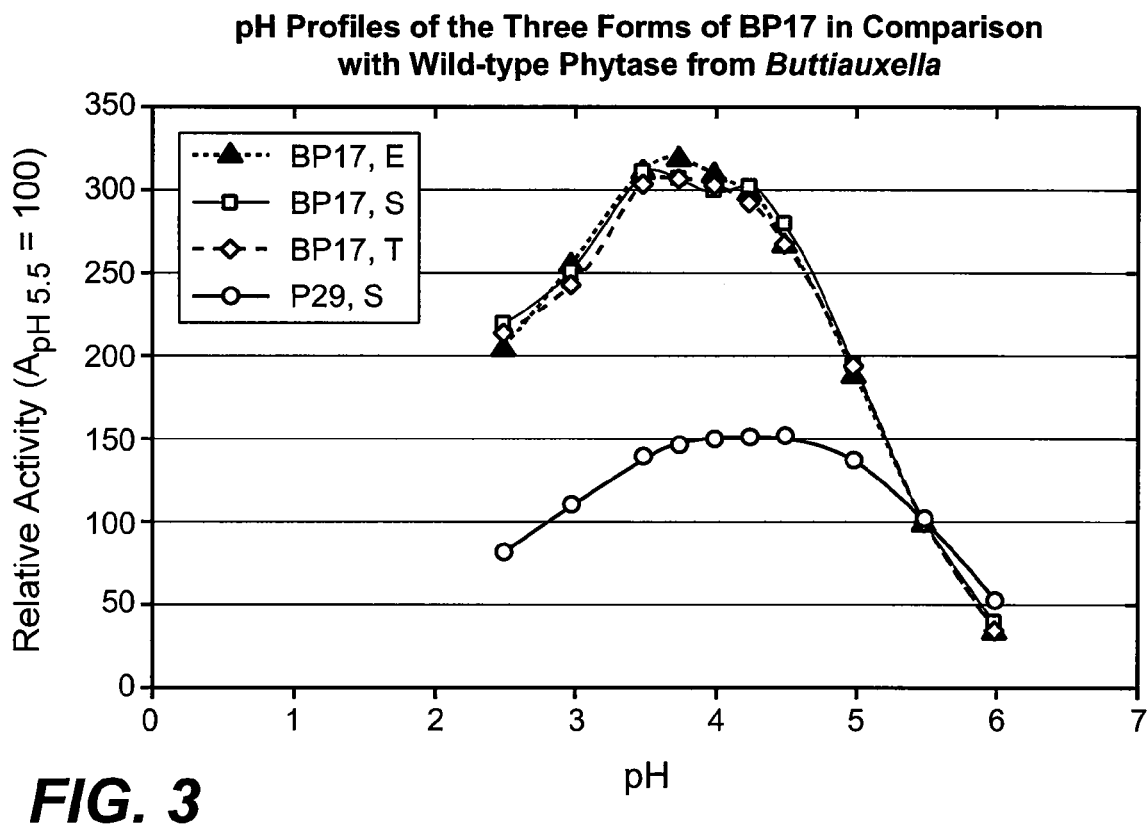
FIG. 3 shows the comparison of the pH profile of BP-17 expressed in *E. coli* and BP-WT as further described in Example 3.

The pH profiles of BP-17 expressed in *E. coli* and wild-type *Buttiauxella* phytase (BP-WT) were measured as follows. Solutions containing 250 mM sodium acetate and 7.5 mM sodium phytate adjusted to pH 6, 5.5, 5, 4.5, 4.25, 4.0, 3.75, 3.5 with hydrochloric acid were used to construct pH profiles in the range pH 3.5 to pH 6.0. Activity of enzymes at pH values of 3.0 and 2.5 was measured in substrate solutions containing 250 mM glycine and 7.5 mM sodium phytase adjusted to the indicated pH with hydrochloric acid. It was found (FIG. 3) that the pH profile of the BP-17 produced in *E. coli* deviated significantly from the pH profile of the wild-type *Buttiauxella* phytase.

Figure 4:
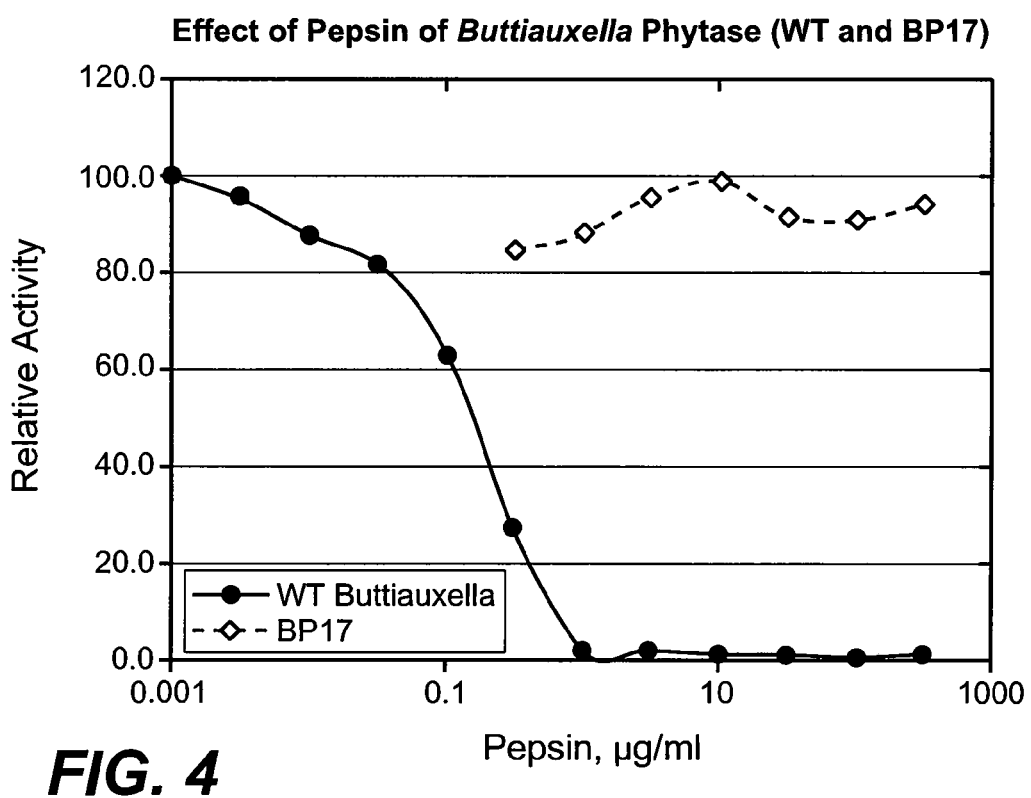
FIG. 4 shows the pepsin resistance of BP-WT and the BP-17 mutant as further described in Example 3.

The enzymes (diluted to about 30 U/ml) were treated with different concentrations of pepsin in 0.25M glycine-hydrochloride buffer, pH 2.0, containing 3 mg/ml BSA at 37° C. for 2 hours. After the incubation, the remaining activity was assayed at pH 5.5. As shown in FIG. 4, BP-17 is essentially stable to pepsin. The high pepsin stability of BP-17 is in contrast with the very low pepsin stability of the wild type *Buttiauxella* phytase, which is essentially completely degraded by 1 μg/ml of pepsin (FIG. 4).

In examples 4-8, wildtype and variant *Buttiauxella* phytase were expressed directly or as a fusion protein in *Trichoderma reesei*. In all cases very strong levels of expression were seen at greater than 10 g/L.

Example 4

Figure 5:
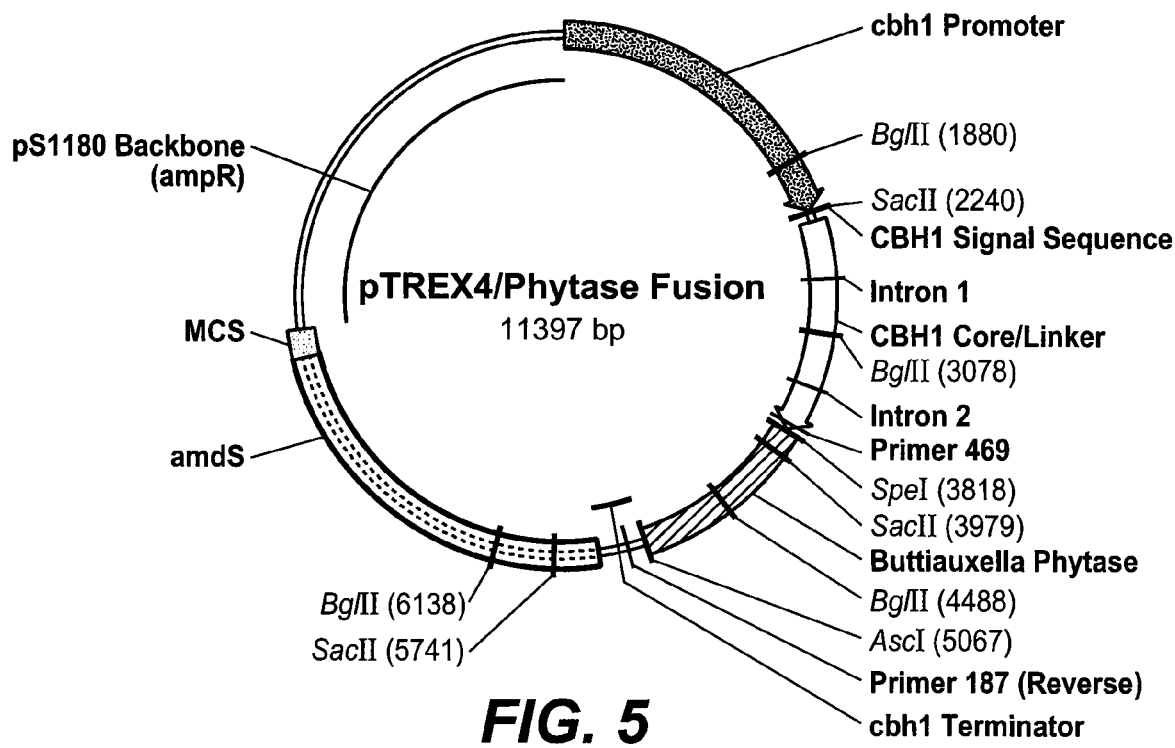
FIG. 5 illustrates the pTREX4/phytase fusion construct as further discussed in Example 4.

Construction and Expression of the Wildtype *Buttiauxella* Phytase in *T. reesei* as a Fusion Protein without a Kex2 Site DNA encoding the wildtype *Buttiauxella* phytase open reading frame was synthesized by GENEART AG (BioPark Josef-Engert-Str. 11, D-93053 Regensburg, Germany). The restriction sites, SpeI and AscI were included for cloning proposes (see Table 4, SEQ ID NO:8). The phytase open reading frame (SEQ ID NO:8) was inserted into the vector, pTrex4, at the Spe1 and Asc1 sites (see FIG. 5). The resulting construct was biolistically transformed into a strain derived from *T. reesei*, using Biolistic PDS-1000/He Particle Delivery System from Bio-Rad (Hercules, Calif.). The transformation protocol used was as described by Foreman (WO 2005/001036). After stable transformants were obtained, these transformants were grown in shake flask cultures for expression analysis of the *Buttiauxella* phytase protein as outlined by Foreman (WO2005/001036). The transformation and expression analysis protocols from WO2005/001036 are incorporated by reference in their entirety herein). After several days of growth on MM acetamide plates, transformants displaying stable morphology were inoculated into 250 ml shake flasks containing 30 ml of Proflo medium. Proflo medium contains: 30 g/L α-lactose; 6.5 g/L $(NH_4)_2SO_4$; 2 g/L $KH_2PO_4$; 0.3 g/L $MgSO_4.7H_2O$; 0.2 g/L $CaCL_2$; 1 ml/L 1000× trace element salt solution; 2 ml/L 10% Tween 80; 22.5 g/L Proflo cottonseed flour (Traders Protein, Memphis, Tenn.); and 0.72 g/L $CaCO_3$. After two days of growth at 28° C. and 225 rpm, 10% of the Proflo culture was transferred to a 250 ml shake flask containing 30 ml of Lactose Defined Media. The composition of Lactose Defined Media was as follows: 5 g/L $(NH_4)_2SO_4$; 33 g/L PIPPS buffer; 9 g/L casamino acids; 4.5 g/L $KH_2PO_4$; 1 g/L $MgSO_4.7H_2O$; 5 ml/L Mazu DF60-P antifoam (mazur Chemicals, Gurnee, Ill.); 1 ml/L 1000× trace element salt solution; pH 5.5. 40 ml/L of 40% (w/v) lactose solution was added to the medium after sterilization. The Lactose Defined medium shake flasks were incubated at 28° C., 225 rpm for 2-3 days. Samples of the culture supernatant were mixed with an appropriate volume of 4× NuPAGE sample buffer (Invitrogen Carlsbad, Calif.) with reducing agent and subjected to polyacrylamide gel electrophoresis (PAGE) using 4-12% NuPAGE precast gels, and MOPS running buffer (Invitrogen Carlsbad, Calif.). The gels were stained for protein detection with Simply Blue Stain (Invitrogen Carlsbad, Calif.). A protein band with an apparent molecular mass of approximately 96 kDa was observed on the stained gel. The expected molecular mass of the fusion protein is approximately 96 kDa. The protein was found to be expressed at greater than 10 g/L.

TABLE 4

DNA sequence of Wildtype *Buttiauxella* phytase containing a SpeI site at the 5' end, and AscI site at the 3' end.

(SEQ ID NO: 8)
ACTAGTAACGACACCCCGCCAGCGGCTACCAGGTCGAGAAGGTCGTCAT

CCTCAGCCGCCACGGAGTCCGCGCCCCCACCAAGATGACCCAGACCATGC

GCGACGTCACCCCCAACACCTGGCCCGAGTGGCCCGTCAAGCTCGGCTAC

ATCACCCCCGCGGCGAGCACCTCATCAGCCTCATGGGCGGCTTCTACCG

CCAGAAGTTCCAGCAGCAGGGCATCCTCAGCCAGGGCTCGTGTCCCACCC

CCAACAGCATCTATGTCTGGGCCGACGTCGACCAGCGCACCCTCAAGACC

GGCGAGGCCTTCCTCGCCGGCCTCGCCCCCCAGTGCGGCCTCACCATCCA

CCACCAGCAGAACCTCGAGAAGGCCGACCCCCTCTTCCACCCCGTCAAGG

CCGGCACCTGCAGCATGGACAAGACCCAGGTCCAGCAGGCCGTCGAGAAG

GAGGCCCAGACCCCCATCGACAACCTCAACCAGCACTACATCCCCTTCCT

CGCCCTCATGAACACCACCCTCAACTTCAGCACCAGCGCCTGGTGCCAGA

AGCACAGCGCCGACAAGAGCTGCGACCTCGGCCTCAGCATGCCCAGCAAG

CTCAGCATCAAGGACAACGGCAACAAGGTCGCCCTCGACGGCGCTATCGG

CCTCAGCTCCACCCTCGCCGAGATCTTCCTCCTCGAGTACGCCCAGGGCA

TGCCTCAGGCTGCCTGGGGCAACATCCACAGCGAGCAGGAGTGGGCCAGC

CTCCTCAAGCTCCACAACGTCCAGTTCGACCTCATGGCCCGCACCCCCTA

CATCGCCCGCCACAACGGCACCCCCCTCCTCCAGGCCATCAGCAACGCCC

TCAACCCCAACGCCACCGAGAGCAAGCTCCCCGACATCAGCCCCGACAAC

AAGATCCTCTTCATCGCCGGCCACGACACCAACATCGCCAACATCGCCGG

CATGCTCAACATGCGCTGGACCCTCCCCGGCCAGCCCGACAACACCCCCC

CCGGCGGCGCTCTCGTCTTTGAGCGCCTCGCCGACAAGTCCGGCAAGCAA

TATGTCTCTGTCAGCATGGTCTACCAGACCCTCGAGCAGCTCCGCAGCCA

GACCCCCCTCAGCCTCAACCAGCCCGCCGGCAGCGTCCAGCTCAAGATCC

CCGGCTGCAACGACCAGACCGCCGAGGGCTACTGCCCCCTCAGCACCTTC

ACCCGCGTCGTCAGCCAGAGCGTCGAGCCCGGCTGCCAGCTCCAGTAAGG

CGCGCC

Example 5

Construction and Expression of the Wildtype *Buttiauxella* Phytase in *T. reesei* as a Fusion Protein with a Kex2 Site The open reading frame of wildtype *Buttiauxella* phytase was amplified by polymerase chain reaction (PCR) using the DNA synthesized by GENEART as the template (see Table 4, SEQ ID NO:8). The PCR machine used was a Peltier Thermal Cycler PTC-200 (MJ Research). The DNA polymerase used in the PCR was HERculase (Stratagene). The primers used to amplify the phytase open reading frame were primer SK667 (forward) 5' CACTACTAGTGTCGCTGTGGAGAAGCG-CAACGACACCCCCGCCAG-3' (SEQ ID NO:9), and primer SK6645' GAGTTCGGCGCGCCTTACTGGA-3' (SEQ ID NO:13). The forward primer contained the amino acid sequence VAVEKR (SEQ ID NO: 10) for efficient cleavage by the Kex2 protease, along with a SpeI site for cloning purposes. The PCR conditions for amplifying the wildtype *Buttiauxella* phytase open reading frame were as follows: Step 1: 94° C. for 1 min. Step 2: 94° C. for 30 sec. Step 3: 58° C. for 30 sec. Step 4: 72° C. for 1 min. Steps 2, 3, and 4 were repeated for an additional 24 cycles. Step 5: 72° C. for 5 min. Step 6: 4° C. for storage. The PCR product was purified using Qiaquick Gel Purification Kit (Qiagen), and digested with restriction enzymes SpeI and AscI (Roche). The digested DNA was purified using Qiaquick PCR Purification Kit, and ligated into the pTrex4 vector at the SpeI and AscI sites (see FIG. 5). The ligation reaction was transformed into TOP 10 chemically competent *E. coli* cells (Invitrogen). See Example 4 for transformation and identification of protein expression. A protein band with an apparent molecular mass of approximately 96 kDa was observed on the stained gel. The expected molecular mass of the fusion protein is approximately 96 kDa. The protein was expressed at greater than 10 g/L.

Example 6

Figure 6:
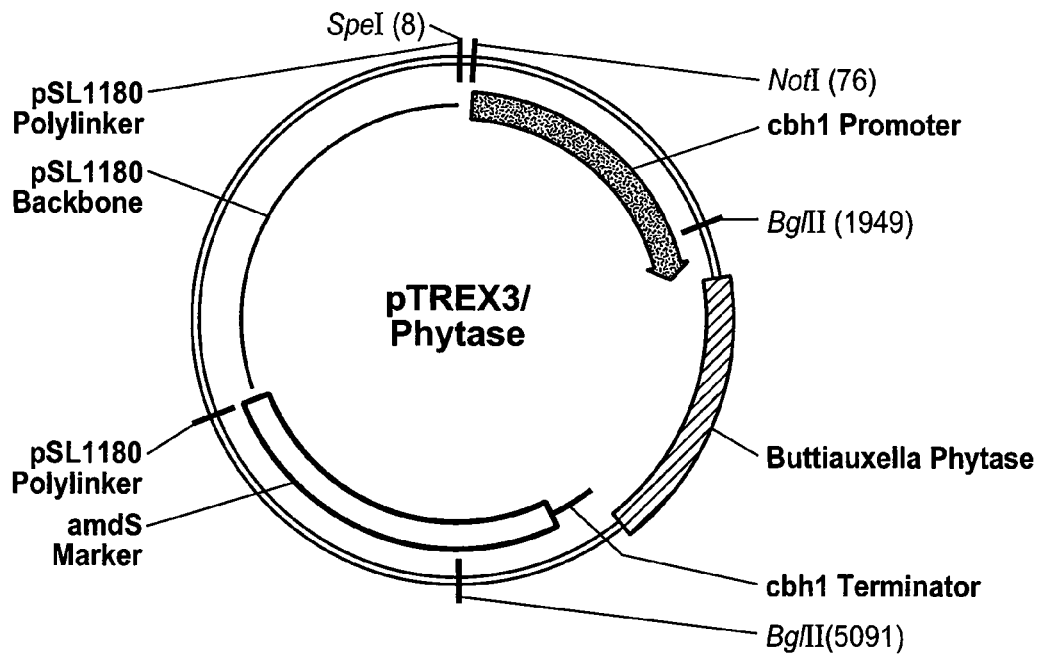
FIG. 6 illustrates the pTREX4/phytase direct construct as further discussed in Example 6.

Construction and Expression of the wildtype *Buttiauxella* Phytase in *T. reesei* as a Direct Construct The open reading frame of wildtype *Buttiauxella* phytase was amplified by polymerase chain reaction (PCR) using the DNA synthesized by GENEART as the template (see Table 5, SEQ ID NO:6). The PCR machine used was a Peltier Thermal Cycler PTC-200 (MJ Research). The DNA polymerase used in the PCR was HERculase (Stratagene). The primers used to amplify the phytase open reading frame were primer SK680 (forward) 5'-CACCATGCAGACCTTCGGT-GCTTTTCTCGTTTCCTTCCTCGCCGCCAGCGG CCTGGCCGCGGCCAACGACACCCCCGCCAGC-3' (SEQ ID NO:11), and primer SK6 5'-CCTTACTGGAGCTG-GCAG-3' (SEQ ID NO:12). The forward primer contained an additional four nucleotides (sequence—CACC) at the 5' end that was required for cloning into the pENTRY/D-TOPO vector (Invitrogen). The PCR conditions for amplifying the wildtype *Buttiauxella* phytase open reading frame were as follows: Step 1: 94° C. for 1 min. Step 2: 94° C. for 30 sec. Step 3: 58° C. for 30 sec. Step 4: 72° C. for 1 min. Steps 2, 3, and 4 were repeated for an additional 24 cycles. Step 5: 72° C. for 5 min. Step 6: 4° C. for storage. The PCR product was purified using Qiaquick Gel Purification Kit (Qiagen). The purified PCR product was initially cloned into the pEN-TRY/D TOPO vector(Invitrogen), and transformed into TOP 10 chemically competent *E. coli* cells (Invitrogen). A pENTR/D-TOPO vector with the correct sequence of the phytase open reading frame was recombined with the pTrex3g vector using LR clonase II (Invitrogen) according to the manufacturers instructions (see FIG. 6). The resulting construct was transformed and protein expression identified as in Example 4. The expected molecular mass of the fusion protein is approximately 46 kDa. The protein was expressed at greater than 10 g/L.

Example 7

Construction and Expression of the BP-17 Variant *Buttiauxella* Phytase in *T. reesei* as a Fusion Protein with a Kex2 Site DNA encoding the BP-17 variant open reading frame was synthesized by GENEART AG (BioPark Josef-Engert-Str. 11, D-93053 Regensburg, Germany) (see Table 5, SEQ ID NO:7). The amino acid sequence VAVEKR (SEQ ID NO:10) was included for Kex2 protease cleavage of the fusion protein, along restriction sites SpeI and AscI for cloning proposes. The phytase open reading frame (SEQ ID NO:7) was inserted into the vector, pTrex4, at the SpeI and AscI sites (see FIG. 5). The resulting construct was transformed and expressed as in Example 4. The expected molecular mass of the fusion protein is approximately 96 kDa. The protein was expressed at greater than 10 g/L.

TABLE 5

DNA sequence of BP-17 variant of *Buttiauxella* phytase containing a SpeI site at the 5' end, and AscI site at the 3' end.

(SEQ ID NO: 7)
ACTAGTGTCGCCGTGGAGAAGCGCAACGACACCCCCGCCAGCGGCTACCA

GGTCGAGAAGGTCGTCATCCTCAGCCGCCACGGCGTCCGCGCCCCTACCA

AGATGACCCAGACCATGCGCGACGTCACCCCCAACACCTGGCCCGAGTGG

CCCGTCAAGCTCGGCTACATCACCCCTCGCGGCGAGCACCTCATCAGCCT

CATGGGCGGCTTCTACCGCCAGAAGTTCCAGCAGCAGGGCATCCTCAGCC

AGGGCTCGTGCCCCACCCCCAACAGCATCTACGTCTGGACCGACGTCGCC

CAGCGCACCCTCAAGACCGGCGAGGCCTTCCTCGCCGGCCTCGCCCCCA

GTGCGGCCTCACCATCCACCACCAGCAGAACCTCGAGAAGGCCGACCCCC

TCTTCCACCCCGTCAAGGCCGGCATCTGCAGCATGGACAAGACCCAGGTC

CAGCAGGCCGTCGAGAAGGAGGCCCAGACCCCCATCGACAACCTCAACCA

GCACTACATCCCCAGCCTCGCCCTCATGAACACCACCCTCAACTTCAGCA

AGAGCCCCTGGTGCCAGAAGCACAGCGCCGACAAGAGCTGCGACCTCGGC

CTCAGCATGCCCAGCAAGCTCAGCATCAAGGACAACGGCAACGAGGTCTC

CCTCGACGGCGCTATCGGCCTCAGCTCCACCCTCGCCGAGATCTTCCTCC

TCGAGTACGCCCAGGGCATGCCTCAGGCCGCCTGGGGCAACATCCACAGC

GAGCAGGAGTGGGCCCTCCTCCTCAAGCTCCACAACGTCTACTTCGACCT

CATGGAGCGCACCCCCTACATCGCCCGCCACAAGGGCACCCCCCTCCTCC

AGGCCATCAGCAACGCCCTCAACCCCAACGCCACCGAGAGCAAGCTCCCC

GACATCAGCCCCGACAACAAGATCCTCTTCATCGCCGGCCACGACACCAA

CATCGCCAACATCGCCGGCATGCTCAACATGCGCTGGACCCTCCCCGGCC

AGCCCGACAACACCCCCCCTGGCGGCGCTCTCGTCTTTGAGCGCCTCGCC

GACAAGTCCGGCAAGCAGTACGTCAGCGTCAGCATGGTCTACCAGACCCT

TABLE 5-continued

DNA sequence of BP-17 variant of *Buttiauxella* phytase containing a SpeI site at the 5' end, and AscI site at the 3' end.

CGAGCAGCTCCGCAGCCAGACCCCCCTCAGCCTCAACCAGCCTGCCGGCA

GCGTCCAGCTCAAGATCCCCGGCTGCAACGACCAGACCGCCGAGGGCTAC

TGCCCCCTCAGCACCTTCACCCGCGTCGTCAGCCAGAGCGTCGAGCCCGG

CTGCCAGCTCCAGTAAGGCGCGCC.

Example 8

Construction and Expression of the BP-17 Variant *Buttiauxella* Phytase in *T. reesei* as a Direct Construct The open reading frame of BP-17 variant *Buttiauxella* phytase was amplified by polymerase chain reaction (PCR) using the DNA synthesized by GENEART as the template (see Table 5, SEQ ID NO:7). The PCR machine used was a Peltier Thermal Cycler PTC-200 (MJ Research). The DNA polymerase used in the PCR was HERculase (Stratagene). The primers used to amplify the phytase open reading frame were primer SK680 (forward) 5'-CACCATGCAGACCT-TCGGTGCTTTTCTCGTTTCCTTCCTCGC-CGCCAGCGG CCTGGCCGCGGCCAACGACAC-CCCCGCCAGC-3' (SEQ ID NO:11), and primer SK6 5'-CCTTACTGGAGCTGGCAG-3'(SEQ ID NO:12). The forward primer contained an additional four nucleotides (sequence—CACC) at the 5' end that was required for cloning into the pENTRY/D-TOPO vector (Invitrogen). The PCR conditions for amplifying the wildtype *Buttiauxella* phytase open reading frame were as follows: Step 1: 94° C. for 1 min. Step 2: 94° C. for 30 sec. Step 3: 58° C. for 30 sec. Step 4: 72° C. for 1 min. Steps 2, 3, and 4 were repeated for an additional 24 cycles. Step 5: 72° C. for 5 min. Step 6: 4° C. for storage. The PCR product was purified using Qiaquick Gel Purification Kit (Qiagen). The purified PCR product was initially cloned into the pENTRY/D TOPO vector (Invitrogen), and transformed into TOP 10 chemically competent *E. coli* cells (Invitrogen). A pENTR/D-TOPO vector with the correct sequence of the phytase open reading frame was recombined with the pTrex3g vector using LR clonase II (Invitrogen) according to the manufacturer's instructions (see FIG. 6). The resulting construct was transformed and expression identified as in Example 4. A protein band with an apparent molecular mass of approximately 46 kDa was observed on the stained gel. The expected molecular mass of the fusion protein is approximately 46 kDa. The protein was found to be expressed at greater than 10 g/L.

What is claimed:

1. A non-naturally occurring phytase variant, wherein the variant
comprises substitution(s) D125A corresponding to the position numbering of SEQ ID NO: 1,
has at least 95% sequence identity inclusive of the variant substitution(s) with amino acid residues 34-446 of SEQ ID NO: 1, and
has phytase enzymatic activity.

2. The phytase variant according to claim 1, wherein the variant further comprises substitutions A122T, T167I, F197S, T209K, A211P, K240E, A242S, S281L, Q289Y, A294E and N303K.

3. The phytase variant according to claim 1, wherein the variant has the sequence of SEQ ID NO: 3.

4. The phytase variant of claim 1, wherein the substitution(s) consists of D125A.

5. A non-naturally occurring phytase variant, wherein the variant comprises substitution(s) D98A corresponding to the position numbering of SEQ ID NO:4, has at least 95% sequence identity to SEQ ID NO:4 and has phytase enzymatic activity.

6. A non-naturally occurring phytase variant, wherein the variant comprises 98% sequence identity to amino acid residues positions 34-446 of SEQ ID NO: 1 and comprises a substitution at position D125 of SEQ ID NO: 1 and has phytase enzymatic activity.

7. A phytase variant according to claim 1 having enhanced thermal stability as compared to the phytase of SEQ ID NO: 2.

8. An enzyme composition comprising the phytase of claim 1.

9. An enzyme composition comprising the phytase of claim 5.

10. The enzyme composition of claim 8, wherein said composition is an animal feed composition.

11. The enzyme composition of claim 8, wherein said composition is used in a starch liquefying process.

12. The enzyme composition of claim 8, wherein said composition is used in an alcohol fermentation process.

13. The enzyme composition of claim 8, further comprising an enzyme selected from the group of glucoamylase, alpha amylase, proteases, cellulases, xylanases and combinations thereof.

14. A fermentation medium comprising the phytase of claim 1 produced from a culture of filamentous fungal cells.

15. The fermentation medium of claim 14, wherein the filamentous fungal cells are *Trichoderma* cells.

16. The fermentation medium of claim 15, wherein the *Trichoderma* cells are *T. reesei*.

17. The fermentation medium of claim 14, wherein the phytase comprises the amino acid sequence of SEQ ID NO: 3.

* * * * *